(12) United States Patent
Aissaoui et al.

(10) Patent No.: US 8,288,429 B2
(45) Date of Patent: Oct. 16, 2012

(54) 2-AZA-BICYCLO[3.3.0]OCTANE DERIVATIVES

(75) Inventors: Hamed Aissaoui, Pulversheim (FR); Christoph Boss, Allschwil (CH); Markus Gude, Allschwil (CH); Ralf Koberstein, Lörrach (DE); Thierry Sifferlen, Wentzwiller (FR); Daniel Trachsel, Bubendorf (CH)

(73) Assignee: Actelion Pharmaceuticals Ltd., Allschwil (CH)

(*) Notice: Subject to any disclaimer, the term of this patent is extended or adjusted under 35 U.S.C. 154(b) by 44 days.

(21) Appl. No.: 12/670,823

(22) PCT Filed: Jul. 25, 2008

(86) PCT No.: PCT/IB2008/052989
§ 371 (c)(1),
(2), (4) Date: Jun. 17, 2010

(87) PCT Pub. No.: WO2009/016564
PCT Pub. Date: Feb. 5, 2009

(65) Prior Publication Data
US 2011/0009461 A1    Jan. 13, 2011

(30) Foreign Application Priority Data

Jul. 27, 2007 (WO) .................. PCT/IB2007/052991

(51) Int. Cl.
*A61K 31/403* (2006.01)
*C07D 209/52* (2006.01)
(52) U.S. Cl. .................. 514/408; 548/465; 548/467
(58) Field of Classification Search .................. 548/465, 548/467
See application file for complete search history.

(56) References Cited

U.S. PATENT DOCUMENTS

| | | |
|---|---|---|
| 5,447,952 A | 9/1995 | Wulfert et al. |
| 2003/0186964 A1 | 10/2003 | Branch et al. |
| 2004/0058921 A1 | 3/2004 | Branch et al. |
| 2006/0040937 A1 | 2/2006 | Branch et al. |
| 2006/0252769 A1 | 11/2006 | Branch et al. |
| 2009/0022670 A1 | 1/2009 | Alvaro et al. |
| 2009/0163485 A1 | 6/2009 | Knust et al. |
| 2010/0016401 A1 | 1/2010 | Aissaoui et al. |
| 2010/0069418 A1 | 3/2010 | Aissaoui et al. |
| 2010/0113531 A1 | 5/2010 | Aissaoui et al. |
| 2010/0168134 A1 | 7/2010 | Breslin et al. |
| 2010/0197733 A1 | 8/2010 | Aissaoui et al. |
| 2010/0204285 A1 | 8/2010 | Aissaoui et al. |
| 2010/0210667 A1 | 8/2010 | Alvaro et al. |
| 2010/0222328 A1 | 9/2010 | Aissaoui et al. |
| 2011/0009401 A1 | 1/2011 | Aissaoui et al. |
| 2011/0039857 A1 | 2/2011 | Aissaoui et al. |

FOREIGN PATENT DOCUMENTS

| | | |
|---|---|---|
| EP | 0058906 | 9/1982 |
| WO | WO 95/29922 | 11/1995 |
| WO | WO 01/96302 | 12/2001 |
| WO | WO 02/44172 | 6/2002 |
| WO | WO 02/089800 | 11/2002 |
| WO | WO 02/090355 | 11/2002 |
| WO | WO 03/002559 | 1/2003 |
| WO | WO 03/002561 | 1/2003 |
| WO | WO 03/032991 | 4/2003 |
| WO | WO 03/041711 | 5/2003 |
| WO | WO 03/051368 | 6/2003 |
| WO | WO 03/051873 | 6/2003 |
| WO | WO 03/062265 | 7/2003 |
| WO | WO 2004/026866 | 4/2004 |
| WO | WO 2004/029050 | 4/2004 |
| WO | WO 2004/041791 | 5/2004 |
| WO | WO 2004/041807 | 5/2004 |
| WO | WO 2004/041816 | 5/2004 |
| WO | WO 2005/092890 | 10/2005 |
| WO | WO 2006/011042 | 2/2006 |
| WO | WO 2008/150364 | 12/2008 |
| WO | WO 2009/143033 | 11/2009 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Dementia [online], retrieved on Sep. 28, 2011. Retrieved from the internet, URL; http://en.wikipedia.org/wiki/Dementia.*
Restless leg syndrome [online]. Retrieved from the internet on Mar. 10, 2012 (URL; http://www.ncbi.nlm.nih.gov/pubmedhealth/PMH0001810/.*

(Continued)

*Primary Examiner* — Shawquia Young
(74) *Attorney, Agent, or Firm* — Hoxie & Associates LLC

(57) ABSTRACT

The invention relates to 2-aza-bicyclo[3.3.0]octane derivatives of Formula (I) wherein A, B, and $R^1$ are as described in the description, and to the use of such compounds, or of pharmaceutically acceptable salts of such compounds, as medicaments, especially as orexin receptor antagonists.

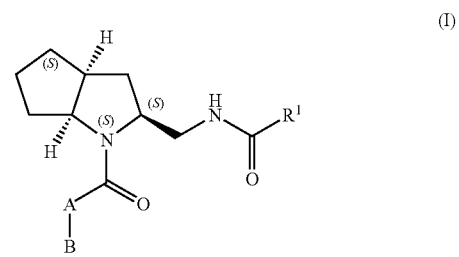

13 Claims, No Drawings

OTHER PUBLICATIONS

Andreani, A., et al., Eur. J. Med. Chem., vol. 17, pp. 271-274, (1982).
Chemelli, R.M., Narcolepsy in orexin Knock Out Mice: Molecular Genetics of Sleep Regulation, Cell, Aug. 20, 1999, vol. 98, 437-451, Cell Press.
Eissenstat, M.A., Aminoalkylindoles: Structure-Activity Relationships of Novel Cannabinoid Mimetics, Journal of Medicinal Chemistry, 1995, vol. 38, 3094-3105, American Chemical Society, Washington DC, USA.
Gould, P.L., Salt Selection for Basic Drugs, International Journal of Pharmaceutics, 1986, vol. 33, 201-217.
March, J., et al., Advanced Organic Chemistry, $4^{th}$ Edition, John Wiley & Sons, pp. 447-449, 919-920, and 1167-1171.
Remington, The Science and Practice of Pharmacy, $21^{st}$ Edition (2005).
Sakurai, T. et al., Orexin & Orexin Receptors: A Family of Hypothalamic Neuropeptides and GProtein-Couples Receptors that Regulate Feeding Behavior, Cell, Feb. 20, 1998, vol. 92, 573-585, Cell Press.
U.S. Appl. No. 12/377,349, filed Feb. 12, 2009, Aissaoui, et al.
U.S. Appl. No. 12/521,453, filed Jun. 26, 2009, Aissaoui, et al.
U.S. Appl. No. 12/667,193, filed Dec. 29, 2009, Aissaoui, et al.
Aissaoui et al; "N-Glycine-Sulfonamides as Potent Dual Orexin 1/Orexin 2 Receptor Antagonists"; Bioorganic & Medicinal Chemistry Letters, vol. 18, pp. 5729-5733, 2008.
Bergman, Bioorganic & Medicinal Chemistry Letters, 2008, vol. 18, 1425-1430.
Bergmeir et al; Tetrahedron, 1999, vol. 55, pp. 8025-8038.
Berry et al; "Cycloaddition Reactions of Thiazolium Azomethine Yilides: Application to Pyrrolo[2,1b]thlazoles"; Organic Letters; 2007; vol. 9, No. 21, 4099-4102.
Bohm et al, "Scaffold Hopping"; Drug Disc. Today Tech, 2004, vol. 1, issue 3, pp. 217-224.
Boss et al; "Biomedical Application of Orexin/Hypocretin Receptor Ligands in Neuroscience"; Journal of Medicinal Chemistry, Vo;1. 52, No. 4, pp. 891-903; 2009.
Boss et al; "Orexin Receptor Antagonism: A New Principle in Neuroscience"; CHIMIA; vol. 62, No. 12, pp. 974-979, 2008.
Cai et al; "Antagonists of the Orexin Receptors, Expert Opinion on Therapeutic Patents", Inform Healthcare, GB, vol. 16, No. 5, pp. 631-646, May 1, 2006.
Cox, Bioorganic & Medicinal Chemistry Letter, 2009, vol. 19, 2997-3001.
Danheiser et al; "Reactions of (Trialkylsilyl)vinylketenes with Lithium Ynolates: A New Benzannulation Strategy"; Organic Letters, 2005, vol. 7, No. 18, 3905-3908.
Eicher et al, "The Chemistry of Heterocycles: Structure, Reactions, Syntheses and Applications", 2nd Edition, 2003, Wiley, ISBN 978-3-527-30720-6.
Gatfield et al; "Orexin Receptor Antagonists: A New Concept in CNS Disorders"; ChemMedChem, vol. 5, pp. 1197-1214, 2010.
Goldstein et al; "A Facile Synthesis of Methyl 2-Substituted-4-benzoxazolecarboxylates", Journal of Heterocyclic Chemistry, 1990, 27, pp. 335-336.
Greene et al, "Protective Groups in Organic Synthesis"; Wiley-Interscience, 1999.
Ishikawa et al; "Cesium Fluoride-Mediated Claisen Rearrangements of Phenyl Propargyl Ethers: Effect of a Substituent on the Phenyl Ring on the Rearrangement", Heterocycles, 1994, 39, No. 1, pp. 371-380.
Jao et al; "Tetrahedron Letters"; 2003; vol. 44, pp. 5033, 5035.
Kawase et al; "The Synthesis of Benzofuran-carboxylic Acids and the Acetylation of their Esters"; Bulletin of the Chemical Society of Japan; 1967, vol. 40, No, 5, 1224-1231, Japan.
Langmead et al; "Characterisation of the Binding of [3H]-SB-674042, a Novel Nonpeptide Antagonist, to the Human Orexin-I Receptor"; British Journal of Pharmacology, vol. 141, pp. 340-346, 2004.
Mohamadi et al; "Total Synthesis and Biological Properties of Novel Antineoplastic (Chloromethyl)furanoindolines: An Asymmetric Hydroboration Mediated Synthesis of he Alkylation Subunits"; Journal of Medicinal Chemistry, 1994, vol. 37, 232-239.
Office Action—Final of U.S. Appl. No. 12/667,193 dated Jul. 11, 2011.
Office Action of U.S. Appl. No. 12/667,193 dated Jan. 19, 2011.
Reetz et al; "Angewandte Chemie"; 1980, vol. 92 (11); pp. 931-933.
Reetz et al; "Chemische Berichte"; 1985, vol. 188 (3); pp. 1050-1057.
Reetz et al; "Direct Geminal Dialkylation of Ketones Using Organotitanium Reagents: A Simple Entry Into Synthetic Tetrahydrocannabinoids"; J. Org. Chem., 1983, vol. 48, pp. 254-255.
Roecker, Current Topic Medicinal Chemistry, 2008, vol. 8, 977-987.
Sifferlen et al; "Novel Pyrazolo-Tetrahydropyridines as Potent Orexin Receptor Antagonists"; Bioorganic & Medicinal Chemistry Letters, vol. 20, pp. 1539-1542, 2010.
Office Action of U.S. Appl. No. 12/311,451 dated Aug. 11, 2011.

* cited by examiner

2-AZA-BICYCLO[3.3.0]OCTANE DERIVATIVES

CROSS REFERENCE TO RELATED APPLICATIONS

This application is a United States Application under 35 U.S.C. 371 claiming benefit of PCT Application No. PCT/IB2008/052989, filed on Jul. 25, 2008, which claims the benefit of PCT Application No. PCT/IB2007/052991, filed on Jul. 27, 2007 the contents of each of which are incorporated herein by reference.

The present invention relates to novel 2-aza-bicyclo[3.3.0] octane derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

The present invention provides 2-aza-bicyclo[3.3.0]octane derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/96302.

The present invention describes for the first time 2-aza-bicyclo[3.3.0]octane derivatives as orexin receptor antagonists.

i) A first aspect of the invention consists of a compound of formula (I) with the stereo genic centers in (1S, 3S, 5S)-configuration Formula (I)

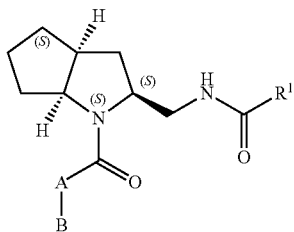

wherein

A represents aryl or heterocyclyl, wherein the aryl or heterocyclyl is unsubstituted or independently mono- or disubstituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or disubstituted phenyl, wherein the substituents are independently selected from the group consisting of $(C_{1-4})$alkyl, $(C_{1-4})$alkoxy, fluorine and chlorine;

B represents an aryl- or heterocyclyl-group, wherein the aryl or heterocyclyl is unsubstituted or independently mono-, di-, or trisubstituted, wherein the substituents are independently selected from the group consisting of $(C_{1-4})$alkyl, $(C_{1-4})$alkoxy, trifluoromethyl, $NR^2R^3$, $NHC(O)CH_3$ and halogen;

$R^1$ represents aryl or heterocyclyl, wherein the aryl or heterocyclyl is unsubstituted or independently mono-, di-, or trisubstituted wherein the substituents are independently selected from the group consisting of $(C_{1-4})$alkyl, $(C_{1-4})$alkoxy, halogen, trifluoromethyl and $NR^2R^3$; or $R^1$ represents a 2,3-dihydro-benzofuranyl- or a 2,3-dihydro-benzo[1,4]dioxinyl-group which groups are unsubstituted or independently mono- or disubstituted with $(C_{1-4})$alkyl, $(C_{1-4})$alkoxy and halogen;

$R^2$ represents hydrogen or $(C_{1-4})$alkyl;

$R^3$ represents hydrogen or $(C_{1-4})$alkyl.

Also part of the invention are compounds of the formula (I) and pharmaceutically acceptable salts thereof.

The term "halogen" means fluorine, chlorine, or bromine, preferably fluorine or chlorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl. Preferred are methyl and ethyl. Most preferred is methyl.

The term "$(C_{2-6})$alkinyl", alone or in combination, means a straight-chain or branched-chain alkinyl group with 2 to 6 carbon atoms. Examples of $(C_{2-6})$alkinyl groups are ethinyl, 1-propinyl, 1-butinyl, 3-methyl-1-butinyl, 1-pentinyl, 3,3-dimethyl-1-butinyl, 3-methyl-1-pentinyl, 4-methyl-1-pentinyl or 1-hexinyl.

The term "$(C_{3-6})$cycloalkyl", alone or in combination, means a cycloalkyl group with 3 to 6 carbon atoms. Examples of $(C_{3-6})$cycloalkyl groups are cyclopropyl, cyclobutyl, cyclopentyl or cyclohexyl. Preferred is cyclopropyl.

The term "$(C_{1-4})$alkoxy", alone or in combination, means a group of the formula $(C_{1-4})$alkyl-O— in which the term "$(C_{1-4})$alkyl" has the previously given significance, such as methoxy, ethoxy, n-propoxy, isopropoxy, n-butoxy, isobutoxy, sec.-butoxy or tert.-butoxy. Preferred are methoxy and ethoxy. Most preferred is methoxy.

The term "aryl", alone or in combination, means a phenyl or a naphthyl group. Preferred is a phenyl group. The aryl group may be unsubstituted or independently mono-, di-, or trisubstituted wherein the substituents are independently selected from the group consisting of $(C_{1-4})$alkyl, $(C_{3-6})$cycloalkyl, $(C_{2-6})$alkinyl, $(C_{1-4})$alkoxy, trifluoromethyl, $NR^2R^3$, $NHC(O)CH_3$, halogen and unsubstituted or independently mono- or disubstituted phenyl, wherein the substituents are independently selected from the group consisting of $(C_{1-4})$alkyl, $(C_{1-4})$alkoxy, fluorine and chlorine.

In case "A" represents "aryl" the term preferably means the above-mentioned group which is unsubstituted or independently mono- or disubstituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or disubstituted phenyl, wherein the substituents are independently selected from the group consisting of $(C_{1-4})$alkyl, $(C_{1-4})$alkoxy, fluorine and chlorine. Preferred examples wherein "A" represents "aryl" are unsubstituted or independently mono- or disubstituted phenyl (preferred monosubstituted phenyl), wherein the substituents are independently selected from the group consisting of $(C_{1-4})$alkyl, $(C_{3-6})$cycloalkyl, $(C_{1-4})$alkoxy and $NR^2R^3$. An example is phenyl. In addition to the above-mentioned substituents, the substituent "A" is also substituted by the substituent "B".

In case "B" represents "aryl" the term preferably means the above-mentioned group which is unsubstituted or independently mono-, di-, or trisubstituted, wherein the substituents are independently selected from the group consisting of $(C_{1-4})$alkyl, $(C_{1-4})$alkoxy, trifluoromethyl, $NR^2R^3$, $NHC(O)CH_3$ and halogen. Preferred examples wherein "B" represents "aryl" are unsubstituted or independently mono-, di-, or trisubstituted phenyl (preferred mono- or disubstituted phenyl), wherein the substituents are independently selected from the group consisting of $(C_{1-4})$alkyl, $(C_{1-4})$alkoxy, trifluoromethyl, $NR^2R^3$, $NHC(O)CH_3$ and halogen (preferred: $(C_{1-4})$alkyl, $NHC(O)CH_3$, trifluoromethyl and halogen). Examples are phenyl, 3-methylphenyl, 4-methylphenyl, 3,5-dimethylphenyl, 2,4-dimethylphenyl, 3,4-dimethylphenyl, 3-fluorophenyl, 4-fluorophenyl, 3-chlorophenyl, 4-bromophenyl, 3,4-difluorophenyl, 3,4-dichlorophenyl, 3-bromo-4-fluorophenyl, 3-acetylaminophenyl and 3-trifluoromethylphenyl. In addition to the above-mentioned substituents, the substituent "B" is attached to the substituent "A".

In case "A" and "B" both represents "aryl" the combination "A-B" preferably means a biphenyl group which is unsubstituted or independently mono- or disubstituted for "A" and unsubstituted or mono-, di- or trisubstituted for "B", wherein the substituents are independently selected from the group consisting of $(C_{1-4})$alkyl, $(C_{1-4})$alkoxy, trifluoromethyl, $NR^2R^3$, $NHC(O)CH_3$ and halogen. Preferred examples wherein "A" and "B" both represents "aryl" are biphenyl groups which are unsubstituted or independently mono- or disubstituted for "A" and unsubstituted or mono-, di- or trisubstituted (preferred mono- or disubstituted) for "B", wherein the substituents are independently selected from the group consisting of $(C_{1-4})$alkyl, $(C_{1-4})$alkoxy, trifluoromethyl and halogen.

In case $R^1$ represents "aryl" the term preferably means the above-mentioned groups which are unsubstituted or independently mono-, di-, or trisubstituted wherein the substituents are independently selected from the group consisting of $(C_{1-4})$alkyl, $(C_{1-4})$alkoxy, halogen, trifluoromethyl and $NR^2R^3$ (preferred: $(C_{1-4})$alkyl, $(C_{1-4})$alkoxy, halogen and trifluoromethyl).

The term "heterocyclyl", alone or in combination, means a 5- to 10-membered monocyclic or bicyclic aromatic ring containing for example 1, 2 or 3 heteroatoms selected from oxygen, nitrogen and sulfur which may be the same or different. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzoisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl or imidazo[2,1-b]thiazolyl. The above-mentioned heterocyclyl groups may also be unsubstituted or independently mono-, di-, or trisubstituted wherein the substituents are independently selected from the group consisting of $(C_{1-4})$alkyl, $(C_{3-6})$cycloalkyl, $(C_{2-6})$alkinyl, $(C_{1-4})$alkoxy, halogen, trifluoromethyl, $NR^2R^3$, $NHC(O)CH_3$ and unsubstituted or independently mono- or disubstituted phenyl, wherein the substituents are independently selected from the group consisting of $(C_{1-4})$alkyl, $(C_{1-4})$alkoxy, fluorine and chlorine.

In case "A" represents "heterocyclyl" the term preferably means the above-mentioned groups which is unsubstituted or independently mono- or disubstituted (preferred unsubstituted or monosubstituted) wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and unsubstituted or independently mono- or disubstituted phenyl, wherein the substituents are independently selected from the group consisting of $(C_{1-4})$alkyl, $(C_{1-4})$alkoxy, fluorine and chlorine.

In a further preferred embodiment, in case "A" represents "heterocyclyl" the term means the above-mentioned groups which is unsubstituted or monosubstituted, wherein the substituent is selected from the group consisting of $(C_{1-4})$alkyl, $(C_{3-6})$cycloalkyl and $NR^2R^3$. Preferred examples wherein "A" represents "heterocyclyl" are unsubstituted or monosubstituted thiazolyl, oxazolyl, pyrimidyl and pyrazinyl (preferred thiazolyl) wherein the substituent is selected from $(C_{1-4})$alkyl, $(C_{3-6})$cycloalkyl or $NR^2R^3$. In addition to the above-mentioned substituents, the substituent "A" is also substituted by the substituent "B".

Further examples wherein "A" represents "heterocyclyl" and one of the substituents is represented by "B" are:

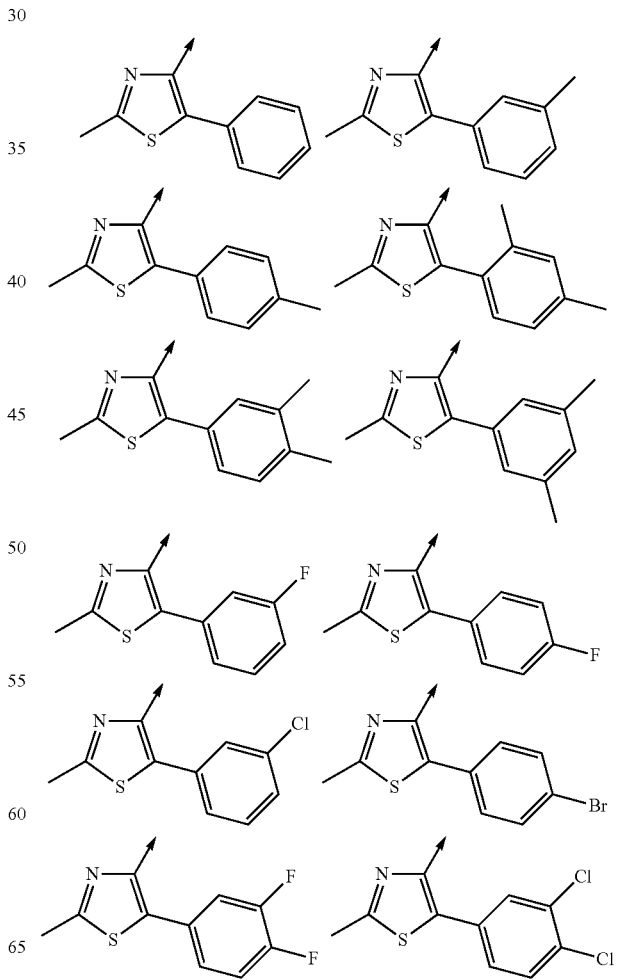

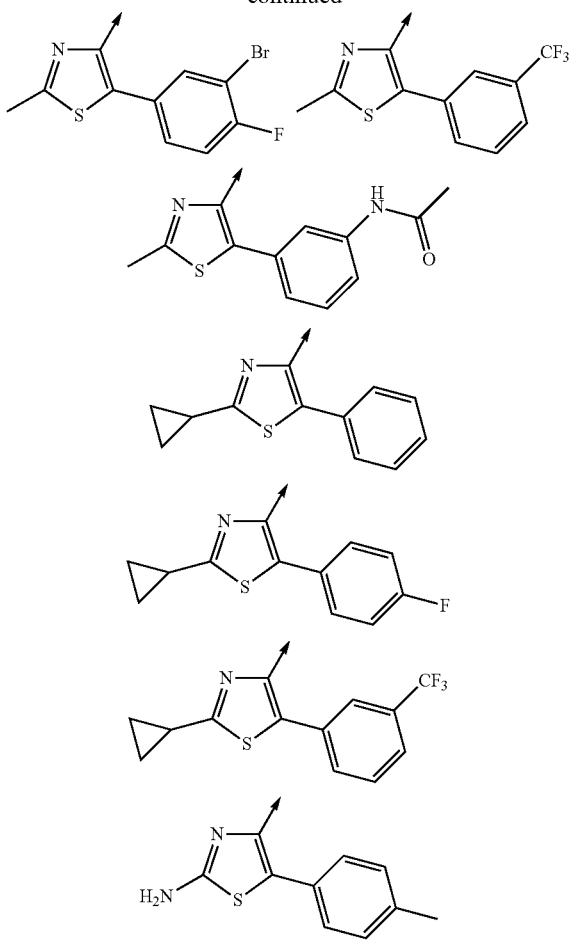

In case "B" represents "heterocyclyl" the term preferably means the above-mentioned groups which is unsubstituted or independently mono-, di-, or trisubstituted (preferred mono- or disubstituted) wherein the substituents are independently selected from the group consisting of $(C_{1-4})$alkyl, $(C_{1-4})$alkoxy, trifluoromethyl, $NR^2R^3$ and halogen (preferred: $(C_{1-4})$alkyl, trifluoromethyl and halogen). In addition to the above-mentioned substituents, the substituent "B" is attached to the substituent "A".

In case $R^1$ represents "heterocyclyl" the term preferably means the above-mentioned groups which is unsubstituted or independently mono-, di-, or trisubstituted (preferred unsubstituted or independently mono- or disubstituted) wherein the substituents are independently selected from the group consisting of $(C_{1-4})$alkyl, $(C_{1-4})$alkoxy, halogen, trifluoromethyl and $NR^2R^3$. In a further preferred embodiment, in case $R^1$ represents "heterocyclyl" the term means the above-mentioned groups which are unsubstituted or independently mono-, di-, or trisubstituted wherein the substituents are independently selected from the group consisting of $(C_{1-4})$alkyl, trifluoromethyl and halogen. In a further preferred embodiment, in case $R^1$ represents "heterocyclyl" the term means the above-mentioned groups which are unsubstituted or independently mono-, or disubstituted wherein the substituent is methyl.

Preferred example wherein $R^1$ represents "heterocyclyl" is:

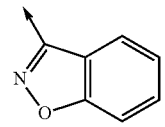

Further preferred example wherein $R^1$ represents "heterocyclyl" is:

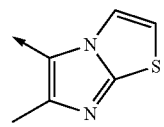

The term "$NR^2R^3$" means for example $NH_2$ and $N(CH_3)_2$.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

ii) A further embodiment of the invention comprises compounds of the formula (I) according to embodiment i), wherein A represents heterocyclyl, wherein the heterocyclyl is unsubstituted or mono-substituted, wherein the substituent is selected from the group consisting of $(C_{1-4})$alkyl, $(C_{3-6})$cycloalkyl or $NR^2R^3$.

iii) A further embodiment of the invention comprises compounds of the formula (I) according to any one of embodiments i) to ii), wherein B represents aryl, wherein the aryl is unsubstituted or independently mono- or disubstituted, wherein the substituents are independently selected from the group consisting of $(C_{1-4})$alkyl, $(C_{1-4})$alkoxy, trifluoromethyl, $NHC(O)CH_3$ and halogen.

iv) A further embodiment of the invention comprises compounds of the formula (I) according to any one of embodiments i) to iii), wherein $R^1$ represents aryl or heterocyclyl, wherein the aryl or heterocyclyl is unsubstituted or independently mono- or disubstituted wherein the substituents are independently selected from the group consisting of $(C_{1-4})$alkyl, $(C_{1-4})$alkoxy and halogen; or $R^1$ represents a 2,3-dihydro-benzo furanyl- or a 2,3-dihydro-benzo[1,4]dioxinyl-group.

v) A further embodiment of the invention comprises compounds of the formula (I) according to any one of embodiments i) to iv), wherein A represents an oxazolyl, a thiazolyl or a pyrimidyl group, which groups are unsubstituted or monosubstituted, wherein the substituent is selected from the group consisting of $(C_{1-4})$alkyl, $(C_{3-6})$cycloalkyl or $NH_2$.

vi) A further embodiment of the invention comprises compounds of the formula (I) according to any one of embodiments i) to v), wherein B represents phenyl, wherein the phenyl is unsubstituted or independently mono- or disubstituted, wherein the substituents are independently selected from the group consisting of $(C_{1-4})$alkyl, trifluoromethyl and halogen.

vii) A further embodiment of the invention comprises compounds of the formula (I) according to any one of embodiments i) to vi), wherein R¹ represents an imidazo[2,1-b]thiazolyl or a benzoisoxazolyl group which groups are unsubstituted or monosubstituted wherein the substituent is selected from the group consisting of $(C_{1-4})$alkyl, trifluoromethyl and halogen; or R¹ represents a 2,3-dihydro-benzofuranyl-group.

viii) A further embodiment of the invention comprises compounds of the formula (I) according to any one of embodiments i) to vii), wherein A represents a thiazolyl group, which group is unsubstituted or monosubstituted, wherein the substituent is selected from the group consisting of $(C_{1-4})$alkyl, $(C_{3-6})$cycloalkyl or NH₂.

ix) A further embodiment of the invention comprises compounds of the formula (I) according to any one of embodiments i) to viii), wherein R² and R³ both represent hydrogen.

Examples of preferred compounds are selected from the group consisting of:

6-Methyl-imidazo[2,1-b]thiazole-5-carboxylic acid [(1S,3S,5 S)-2-(2-methyl-5-p-tolyl-thiazole-4-carbonyl)-2-azabicyclo[3.3.0]octane-3-ylmethyl]-amide;

6-Methyl-imidazo[2,1-b]thiazole-5-carboxylic acid [(1S,3S,5S)-2-(2-amino-5-p-tolyl-thiazole-4-carbonyl)-2-azabicyclo[3.3.0]octane-3-ylmethyl]-amide;

6-Methyl-imidazo[2,1-b]thiazole-5-carboxylic acid {(1S,3S,5S)-2-[5-(3-chlorophenyl)-2-methyl-thiazole-4-carbonyl]-2-azabicyclo[3.3.0]octane-3-ylmethyl}-amide;

6-Methyl-imidazo[2,1-b]thiazole-5-carboxylic acid {(1S,3S,5S)-2-[5-(4-fluorophenyl)-2-methyl-thiazole-4-carbonyl]-2-azabicyclo[3.3.0]octane-3-ylmethyl}-amide;

6-Methyl-imidazo[2,1-b]thiazole-5-carboxylic acid {(1S,3S,5S)-2-[5-(3-fluorophenyl)-2-methyl-thiazole-4-carbonyl]-2-azabicyclo[3.3.0]octane-3-ylmethyl}-amide;

6-Methyl-imidazo[2,1-b]thiazole-5-carboxylic acid {(1S,3S,5S)-2-[2-cyclopropyl-5-(4-fluoro-phenyl)-thiazole-4-carbonyl]-2-azabicyclo[3.3.0]octane-3-ylmethyl}-amide;

6-Methyl-imidazo[2,1-b]thiazole-5-carboxylic acid {(1S,3S,5S)-2-[2-cyclopropyl-5-(3-trifluoromethyl-phenyl)-thiazole-4-carbonyl]-2-azabicyclo[3.3.0]octane-3-ylmethyl}-amide;

Benzo[d]isoxazole-3-carboxylic acid [(1S,3S,5S)-2-(2-methyl-5-p-tolyl-thiazole-4-carbonyl)-2-azabicyclo[3.3.0]octane-3-ylmethyl]-amide;

Benzo[d]isoxazole-3-carboxylic acid {(1S,3S,5S)-2-[5-(3-chloro-phenyl)-2-methyl-thiazole-4-carbonyl]-2-azabicyclo[3.3.0]octane-3-ylmethyl}-amide;

Benzo[d]isoxazole-3-carboxylic acid {(1S,3S,5S)-2-[5-(3-fluoro-phenyl)-2-methyl-thiazole-4-carbonyl]-2-azabicyclo[3.3.0]octane-3-ylmethyl}-amide;

Benzo[d]isoxazole-3-carboxylic acid [(1S,3S,5S)-2-(2-cyclopropyl-5-phenyl-thiazole-4-carbonyl)-2-azabicyclo[3.3.0]octane-3-ylmethyl]-amide;

2,3-Dihydro-benzofuran-4-carboxylic acid {(1S,3S,5S)-2-[5-(3-chloro-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3-fluoro-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(4-fluoro-phenyl)-2-methyl-thiazole-4-carbonyl]-2-azabicyclo[3.3.0]octane-3-ylmethyl}-amide;

2,3-Dihydro-benzofuran-4-carboxylic acid [(1S,3S,5S)-2-(2-methyl-5-m-tolyl-thiazole-4-carbonyl)-2-azabicyclo[3.3.0]octane-3-ylmethyl]-amide;

2,3-Dihydro-benzofuran-4-carboxylic acid {(1S,3S,5S)-2-[2-methyl-5-(3-trifluoromethyl-phenyl)-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(4-bromo-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3,5-dimethyl-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3-bromo-4-fluoro-phenyl)-2-methyl-thiazole-4-carbonyl]-2-azabicyclo [3.3.0]octane-3-ylmethyl}-amide;

2,3-Dihydro-benzofuran-4-carboxylic acid {(1S,3S,5S)-2-[5-(3,4-difluoro-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(2,4-dimethyl-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3,4-dichloro-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3,4-dimethyl-phenyl)-2-methyl-thiazole-4-carbonyl]-2-azabicyclo[3.3.0]octane-3-ylmethyl}-amide;

2,3-Dihydro-benzofuran-4-carboxylic acid {(1S,3S,5S)-2-[5-(3-acetylamino-phenyl)-2-methyl-thiazole-4-carbonyl]-2-azabicyclo[3.3.0]octane-3-ylmethyl}-amide;

2,3-Dihydro-benzofuran-4-carboxylic acid [(1S,3S,5S)-2-(2-methyl-5-phenyl-thiazole-4-carbonyl)-2-azabicyclo[3.3.0]octane-3-ylmethyl]-amide; and 2,3-Dihydro-benzofuran-4-carboxylic acid [(1S,3S,5S)-2-(2-cyclopropyl-5-phenyl-thiazole-4-carbonyl)-2-azabicyclo[3.3.0]octane-3-ylmethyl]-amide.

The compounds according to formula (I) may be used for the preparation of a medicament, and are suitable, for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; postoperative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

The compounds according to formula (I) may be used for the preparation of a medicament, and are suitable, for the prevention or treatment of diseases selected from the group consisting of all types of sleep disorders, of stress-related syndromes, of psychoactive substance use, abuse, seeking and reinstatement, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Drinking disorders include polydipsias in psychiatric disorders and all other types of excessive fluid intake.

Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance. Psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds according to formula (I) may be used for the preparation of a medicament, and are suitable, for the prevention or treatment of diseases selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of formula (I) may be used for the preparation of a medicament, and are suitable, for the prevention or treatment of diseases selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) may be used for the preparation of a medicament, and are suitable, for the prevention or treatment of diseases selected from the group consisting of eating disorders that comprise metabolic dysfunction; dysregulated appetite control; compulsive obesities; emeto-bulimia or anorexia nervosa.

In another preferred embodiment of the invention compounds of formula (I) may be used for the preparation of a medicament, and are suitable, for the prevention or treatment of diseases selected from the group consisting of psychoactive substance use, abuse, seeking and reinstatement that comprise all types of psychological or physical addictions and their related tolerance and dependence components.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I) and their pharmaceutically acceptable salts can be used as medicaments, e.g. in the form of pharmaceutical compositions for enteral or parental administration.

A further aspect of the invention is a process for the preparation of compounds of formula (I). Compounds according to formula (I) of the present invention can be prepared according to the general sequence of reactions outlined in the schemes below wherein A, B and $R^1$ are as defined in the description of formula (I). The compounds obtained may also be converted into pharmaceutically acceptable salts thereof in a manner known per se.

In general, all chemical transformations can be performed according to well-known standard methodologies as described in the literature or as described in the procedures below.

Preparation of Compounds of Formula (I):

Scheme 1: Synthesis of compounds of formula (I), wherein A, B and $R^1$ are as defined above

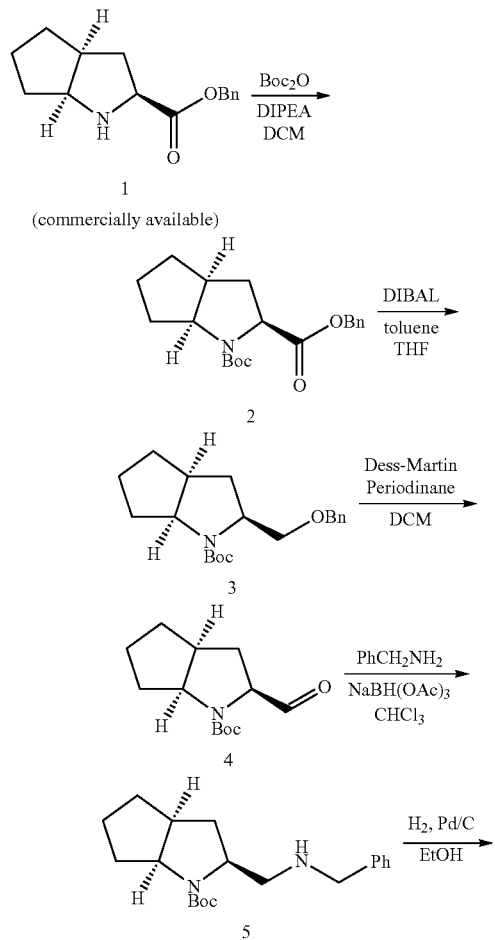

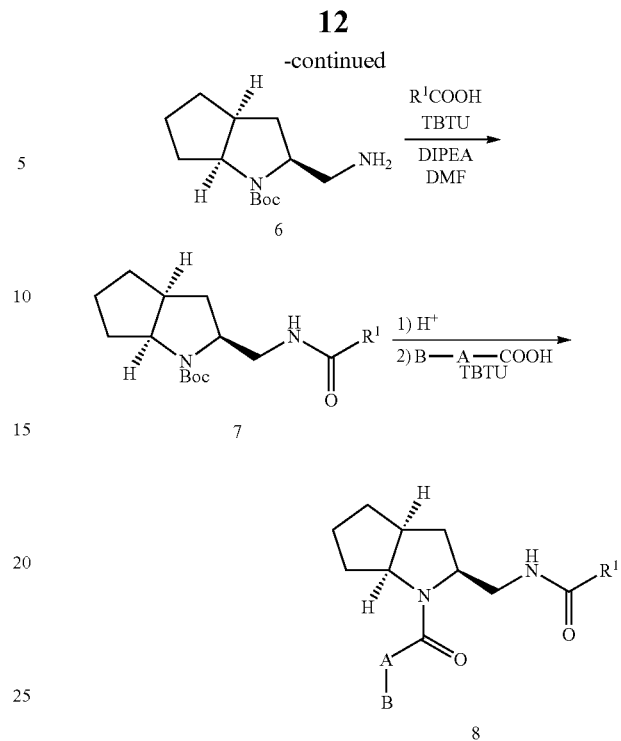

The first step in the synthesis of 2-aza-bicyclo[3.3.0]octane derivatives of formula (I) was the protection of the nitrogen atom of (1S,3S,5S)-2-azabicyclo[3.3.0]octane-3-carboxylate with $Boc_2O$ to give compound (2) which was reduced to alcohol (3) by treatment with DIBAL at low temperatures. The alcohol (3) was oxidized to the corresponding aldehyde (4) with a oxidizing agent like e.g. Dess-Martin periodinane. After reductive amination of (4) with benzylamine in the presence of a reducing agent like sodium triacetoxyborohydride the benzyl group of intermediate (5) was removed by hydrogenolysis to yield the primary amine (6). The acylation of (6) with a carboxylic acid $R^1COOH$ in the presence of a coupling reagent like TBTU resulted in the formation of amides (7) which after removal of the Boc-group were transferred to compounds of formula (I) by amide coupling (e.g. B-A-COOH, TBTU).

Thiazole-4-carboxylic acid derivatives of formula B-A-COOH were for instance synthesised according to scheme 2.

Scheme 2: Synthesis of thiazole-4-carboxylic acid derivatives, wherein B is as defined above, and R is $(C_{1-4})$alkyl, $(C_{3-6})$cycloalkyl or $NR^2R^3$, wherein $R^2$ and $R^3$ represent independently from each other hydrogen or $(C_{1-4})$alkyl

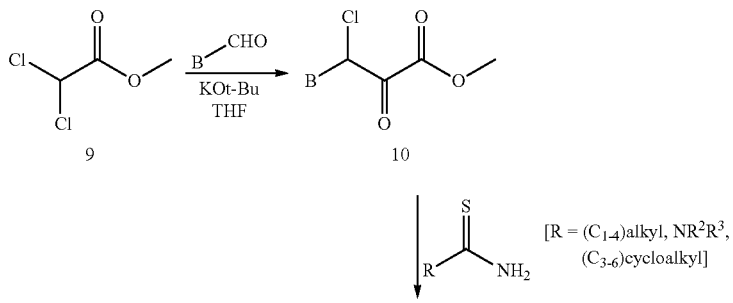

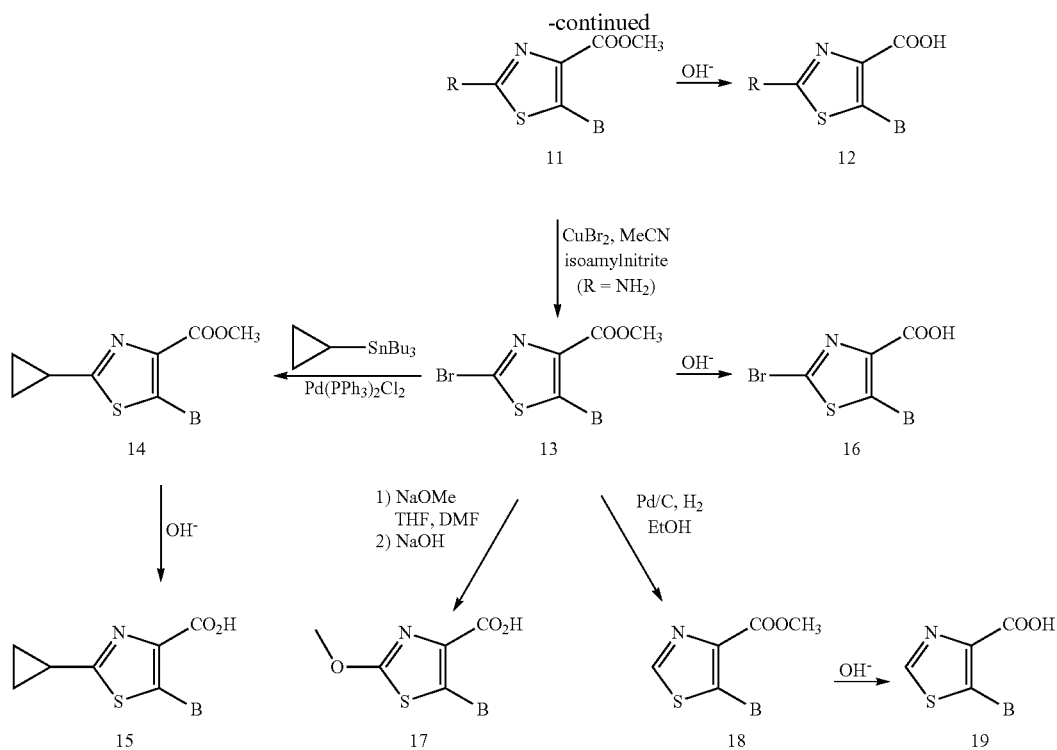

By reaction of methyl dichloroacetate (9; commercially available) with an aldehyde in the presence of a base like potassium tert.-butoxide the α-oxo-ester derivatives (10) were obtained which were transformed in a reaction with thioamides [R=($C_{1-4}$)alkyl or ($C_{3-6}$)cycloalkyl] to 2-alkyl- or 2-cycloalkylsubstituted thiazole derivatives (11) or in a reaction with thioureas (R=$NR^2R^3$) to 2-amino-substituted thiazole derivatives (11). Saponification of the ester function with an aqueous solution of e.g. sodium hydroxide in a solvent like methanol resulted in the formation of the desired carboxylic acids (12, R=($C_{1-4}$)alkyl, ($C_{3-6}$)cycloalkyl or $NR^2R^3$). 2-Bromo-thiazole derivatives (13) were for instance obtained by reaction of the respective 2-amino-thiazole derivative (11, R=$NH_2$) with isoamylnitrite in the presence of copper(II) bromide. The ester derivatives (13) were transferred in a palladium catalyzed reaction with cyclopropyl-tin derivatives (commercially available) to compounds (14) which after saponification gave the respective carboxylic acids (15). The 2-bromo-thiazole derivative (13) might additionally be saponified to the respective carboxylic acids (16) as described above or transferred to 2-methoxy substituted analogues (17) by reaction with sodium methoxide and subsequent saponification with sodium hydroxide. In addition compounds (19) which are unsubsituted in 2-position might be synthesized by hydrogenation of (13) with hydrogen in the presence of palladium on charcoal and subsequent saponification of the intermediate ester (18). ($C_{3-6}$)cycloalkyl-substituted thioamides used in the synthesis of (11) are commercially available, or were obtained by reaction of the respective carboxamide with Lawesson's reagent (see also experimental part A.1.6). Aldehydes B—CHO may be commercially available or synthesized by any procedure known from the literature like for instance reduction of the respective carboxylic acid or their different derivatives with a reducing agent, by reduction of the respective nitrile or by oxidation of benzylic alcohols and their heterocyclic analogues with oxidating agents (e.g.: J. March, *Advanced Organic Chemistry*, 4$^{th}$ edition, John Wiley & Sons, p. 447-449, 919-920 and 1167-1171).

Imidazo[2,1-b]thiazole-carboxylic acid derivatives of formula $R^1$—COOH, if not commercially available, might be synthesised according to one of the different pathways shown in scheme 3.

Scheme 3: Synthesis of imidazo[2,1-b]thiazole-carboxylic acid derivatives wherein R is methyl or ethyl, $R^a$ is hydrogen or methyl, $R^b$ is hydrogen or methyl, X is chlorine or bromine, and Y is chlorine or trifluoromethyl Pathway A:

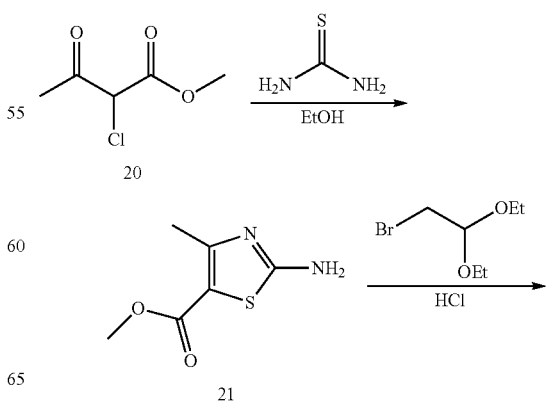

Pathway B:
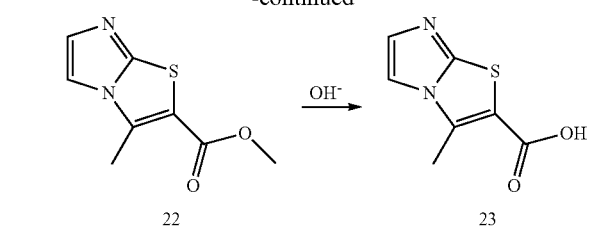
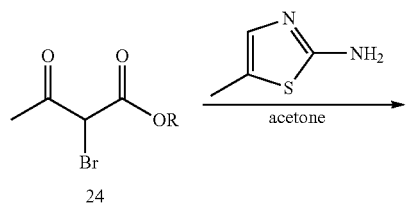
Pathway C:
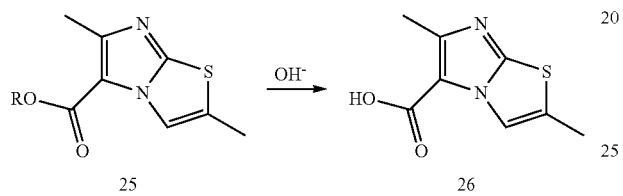
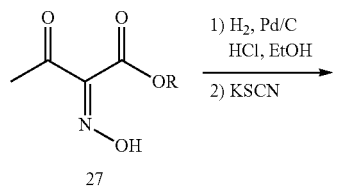 + 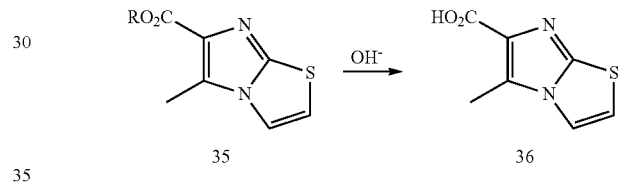
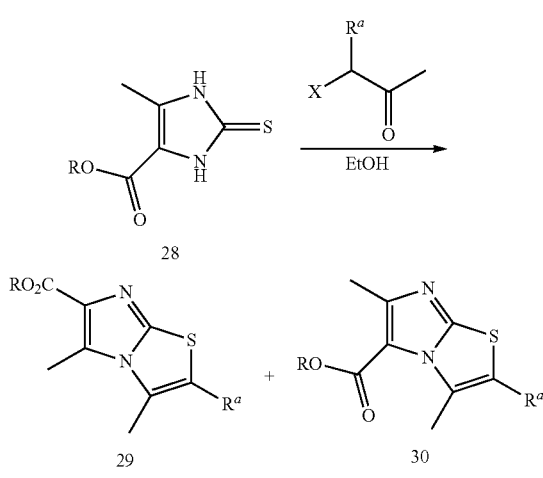
Pathway D:
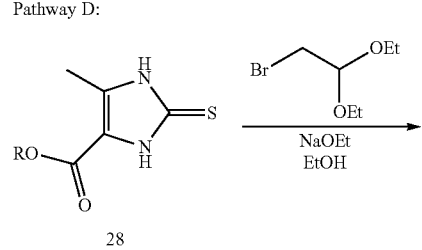
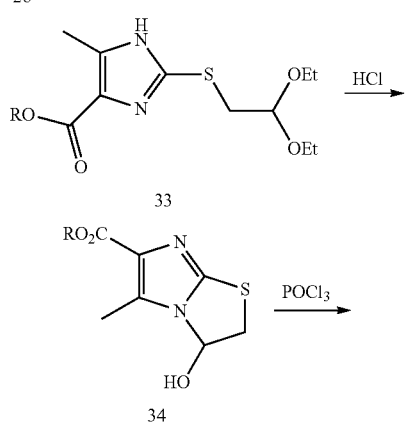
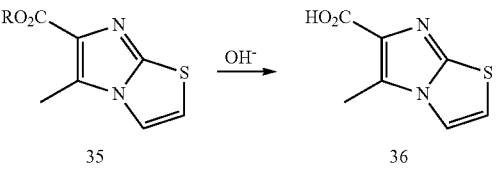
Pathway E:
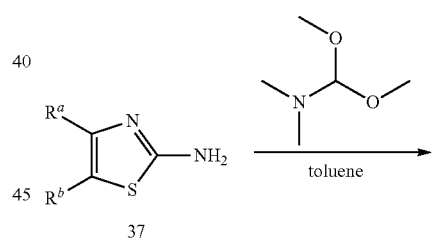
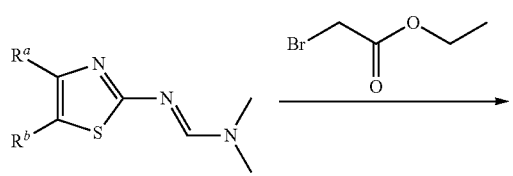
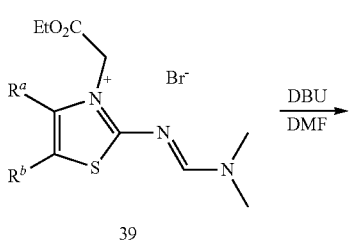

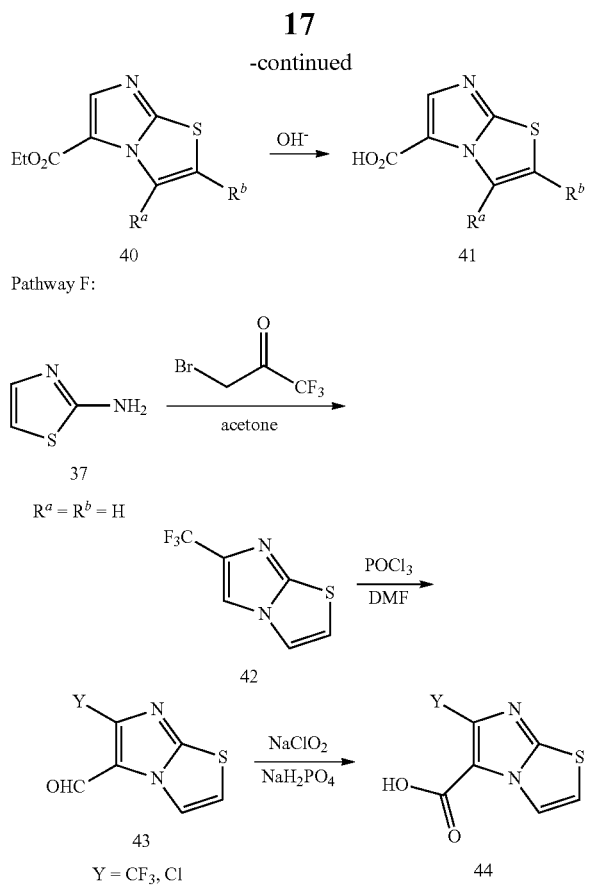

Pathway F:

$R^a = R^b = H$

Y = CF₃, Cl

Following pathway A imidazo[2,1-b]thiazole-carboxylic acid derivatives were synthesized starting from 2-chloro-3-oxo-butyric acid methyl ester (20; commercially available) by reaction with thiourea (commercially available) in a solvent like ethanol at elevated temperatures. The obtained amino-thiazole (21) was converted to the imidazo[2,1-b]thiazole derivative (22) by alkylation and subsequent cyclization with bromoacetaldehyde diethyl acetal in the presence of an acid like concentrated hydrochloric acid. By saponification of (22) with for instance sodium hydroxide in solvents like THF and MeOH the desired acids (23) were obtained.

An alternative approach (pathway B) started with the reaction of 2-bromo-3-oxo-butyric acid ester (24; commercially available) with 2-amino-5-methyl-thiazole (commercially available) in a solvent like acetone to give the imidazo[2,1-b]thiazole derivative (25) which was transformed to the desired acid (26) by saponification with for instance sodium hydroxide in solvents like THF and MeOH.

By hydrogenation of 2-hydroxyimino-3-oxo-butyric acid ester (27; commercially available) in the presence of palladium on charcoal under acidic conditions (e.g. HCl in EtOH) and subsequent reaction with potassium thiocyanate the imidazole derivative (28) was obtained which was transferred to a mixture of the two possible isomers (29) and (30) by reaction with the respective α-halogenated propanone (commercially available) or butanone derivative (pathway C; commercially available).

After separation of the isomers (29) and (30) by chromatography the desired imidazo[2,1-b]thiazole-carboxylic acid derivatives (31) and (32) were obtained by saponification with for instance sodium hydroxide in solvents like THF and MeOH.

Alternatively (pathway D) the imidazole derivative (28) may be transferred to the acetal (33) by alkylation with bromoacetaldehyde diethyl acetal (commercially available) in the presence of a base like sodium ethoxide. Cyclization under acidic conditions (e.g. aqueous hydrochloric acid) and dehydration of the intermediate (34) with for instance phosphorus oxychloride led to ester (35) which was transformed to the desired acid (36) by saponification with for instance sodium hydroxide in solvents like THF and MeOH.

In still an alternative procedure (pathway E) the respective amino-thiazole (37; commercially available) was converted to the formamidine derivative (38) by heating (37) with N,N-dimethylformamide dimethylacetale (commercially available) in a solvent like toluene. After alkylation with ethyl bromoacetate (commercially available) the respective thiazolium bromide (39) was cyclised with DBU to yield the ester (40) which was saponified to the desired acid (41) with for instance sodium hydroxide in solvents like THF and MeOH.

Finally pathway F started with the alkylation of 2-aminothiazole (;commercially available) with 3-bromo-1,1,1-trifluoroacetone (commercially available) to yield the trifluoromethyl-substituted imidazo[2,1-b]thiazole derivative (42) which was formylated to the aldehyde (43) by reaction with phosphorus oxychloride in a solvent like DMF. By oxidation of aldehyde (43) with sodium chlorite the desired imidazo[2,1-b]thiazole-carboxylic acid (44, Y=CF₃) was obtained. In analogy the commercially available chlorinated aldehyde (43, Y=Cl) was oxidized to the acid (44, Y=Cl).

EXPERIMENTAL SECTION

Abbrevations (As Used Herein and in the Description Above):

| | |
|---|---|
| Ac | Acetyl as in OAc: acetate |
| Boc | tert-Butoxycarbonyl |
| BSA | Bovine serum albumine |
| Bu | n-Butyl |
| CHO | Chinese hamster ovary |
| conc. | Concentrated |
| d | Day(s) |
| DBU | 1,8-Diazabicyclo[5.4.0]undec-7-ene |
| DCM | Dichloromethane |
| DIBAL | Diisobutylaluminium hydride |
| DIPEA | Diisopropylethylamine |
| DMAP | 4-Dimethylaminopyridine |
| DMF | N,N-Dimethylformamide |
| eq | Equivalent(s) |
| ES | Electron spray |
| Et | Ethyl |
| EtOH | Ethanol |
| EtOAc | Ethyl acetate |
| Ether | Diethylether |
| FCS | Foatal calf serum |
| FLIPR | Fluorescent imaging plate reader |
| h | Hour(s) |
| HBSS | Hank's balanced salt solution |
| HEPES | 4-(2-hydroxyethyl)-piperazine-1-ethanesulfonic acid |
| HPLC | High performance liquid chromatography |
| KOt-Bu | Potassium tertiary (tert.) butoxide |
| LC | Liquid chromatography |
| M | Molar(ity) |
| Me | Methyl |
| MeCN | Acetonitrile |
| MeOH | Methanol |
| min | Minute(s) |
| MS | Mass spectroscopy |
| Ph | Phenyl |
| prep. | Preparative |
| RT | Room temperature |
| sat | Saturated |

-continued

| $t_R$ | Retention time |
| --- | --- |
| TBTU | O-Benzotriazol-1-yl-N,N,N',N'-tetramethyluronium tetrafluoroborate |
| TFA | Trifluoroacetic acid |
| THF | Tetrahydrofuran |

I—Chemistry

The following examples illustrate the preparation of pharmacologically active compounds of the invention but do not at all limit the scope thereof.

All temperatures are stated in ° C.

Compounds are characterized by:

¹H-NMR: 300 MHz Varian Oxford or 400 MHz Bruker Avance; chemical shifts are given in ppm relative to the solvent used; multiplicities: s=singlet, d=doublet, t=triplet, m=multiplet, b=broad, coupling constants are given in Hz;

LC-MS: Agilent 1100 series with DAD and MS detection (MS: Finnigan single quadrupole); columns (4.6×50 mm, 5 μm): Zorbax SB-AQ, Zorbax Extend C18 or Waters XBridge C18; conditions:

basic: eluent A: MeCN, eluent B: conc. $NH_3$ in water (1.0 mL/L), 5% to 95% $CH_3CN$;

acidic: eluent A: MeCN, eluent B: TFA in water (0.4 mL/L), 5% to 95% $CH_3CN$), $t_R$ is given in min;

Compounds are purified by column chromatography on silica gel or by preparative HPLC using RP-$C_{18}$ based columns with MeCN/water gradients and formic acid or ammonia additives.

A. Preparation of Precursors and Intermediates:

A.1 Synthesis of thiazole-4-carboxylic acid Derivatives

A.1.1 Synthesis of 3-chloro-2-oxo-propionic ester Derivatives (General Procedure)

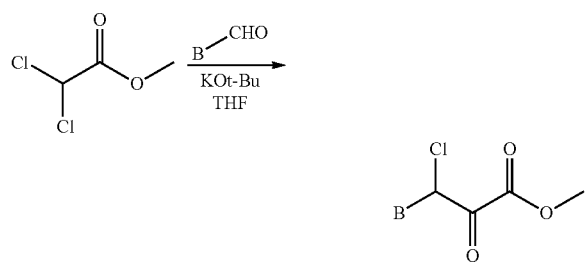

A solution of the respective aldehyde (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aqueous layer is extracted twice with DCM. The combined organic layers are washed with ice-cold water and brine, dried over $MgSO_4$ and concentrated in vacuo to give the desired α-oxo-ester which is used without further purification.

3-chloro-2-oxo-3-p-tolyl-propionic acid methyl ester prepared by reaction of 4-methyl-benzaldehyde with methyl dichloroacetate.

3-chloro-3-(3-fluoro-phenyl)-2-oxo-propionic acid methyl ester prepared by reaction of 3-fluoro-benzaldehyde with methyl dichloroacetate.

3-chloro-3-(4-fluoro-phenyl)-2-oxo-propionic acid methyl ester prepared by reaction of 4-fluoro-benzaldehyde with methyl dichloroacetate.

3-chloro-3-(3-chloro-phenyl)-2-oxo-propionic acid methyl ester prepared by reaction of 3-chloro-benzaldehyde with methyl dichloro-acetate.

3-Chloro-2-oxo-3-m-tolyl-propionic acid methyl ester prepared by reaction of 3-methyl-benzaldehyde with methyl dichloro-acetate.

3-chloro-2-oxo-3-(3-trifluoromethyl-phenyl)-propionic acid methyl ester prepared by reaction of 3-trifluoromethyl-benzaldehyde with methyl dichloro-acetate.

3-(4-Bromo-phenyl)-3-chloro-2-oxo-propionic acid methyl ester prepared by reaction of 4-bromo-benzaldehyde with methyl dichloro-acetate.

3-Chloro-3-(3,5-dimethyl-phenyl)-2-oxo-propionic acid methyl ester prepared by reaction of 3,5-dimethyl-benzaldehyde with methyl dichloro-acetate.

3-(3-Bromo-4-fluoro-phenyl)-3-chloro-2-oxo-propionic acid methyl ester prepared by reaction of 3-bromo-4-fluoro-benzaldehyde with methyl dichloro-acetate.

3-Chloro-3-(3,4-difluoro-phenyl)-2-oxo-propionic acid methyl ester prepared by reaction of 3,4-difluoro-benzaldehyde with methyl dichloro-acetate.

3-Chloro-3-(2,4-dimethyl-phenyl)-2-oxo-propionic acid methyl ester prepared by reaction of 2,4-dimethyl-benzaldehyde with methyl dichloro-acetate.

3-Chloro-3-(3,4-dichloro-phenyl)-2-oxo-propionic acid methyl ester prepared by reaction of 3,4-dichloro-benzaldehyde with methyl dichloro-acetate.

3-Chloro-3-(3,4-dimethyl-phenyl)-2-oxo-propionic acid methyl ester prepared by reaction of 3,4-dimethyl-benzaldehyde with methyl dichloro-acetate.

3-Chloro-2-oxo-3-phenyl-propionic acid methyl ester prepared by reaction of benzaldehyde with methyl dichloro-acetate.

3-Chloro-3-(3-nitro-phenyl)-2-oxo-propionic acid methyl ester prepared by reaction of 3-nitro-benzaldehyde with methyl dichloro-acetate.

A.1.2 Synthesis of thiazole-4-carboxylic acid methyl ester Derivatives (General Procedure)

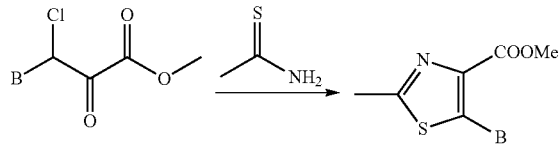

A solution of thioacetamide (132 mmol, 1.0 eq) in MeCN (250 mL) is added to a mixture of the respective α-oxo-ester (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the desired thiazole derivatives as a white solid.

2-methyl-5-p-tolyl-thiazole-4-carboxylic acid methyl ester prepared by reaction of 3-chloro-2-oxo-3-p-tolyl-propionic acid methyl ester with thioacetamide. LC-MS: $t_R$=0.92 min; $[M+H]^+$=248.2.

5-(3-fluoro-phenyl)-2-methyl-thiazole-4-carboxylic acid methyl ester prepared by reaction of 3-chloro-3-(3-fluoro-phenyl)-2-oxo-propionic acid methyl ester with thioacetamide. LC-MS: $t_R$=0.91 min; $[M+H]^+$=252.1.

5-(4-fluoro-phenyl)-2-methyl-thiazole-4-carboxylic acid methyl ester prepared by reaction of 3-chloro-3-(4-fluoro-phenyl)-2-oxo-propionic acid methyl ester with thioacetamide. $^1$H-NMR (CDCl$_3$): δ=2.75 (s, 3H); 3.84 (s, 3H); 7.10 (m, 2H); 7.47 (m, 2H).

5-(3-chloro-phenyl)-2-methyl-thiazole-4-carboxylic acid methyl ester prepared by reaction of 3-chloro-3-(3-chloro-phenyl)-2-oxo-propionic acid methyl ester with thioacetamide. LC-MS: $t_R$=0.95 min; $[M+H]^+$=268.0.

2-Methyl-5-m-tolyl-thiazole-4-carboxylic acid methyl ester prepared by reaction of 3-Chloro-2-oxo-3-m-tolyl-propionic acid methyl ester with thioacetamide. LC-MS: $t_R$=0.98 min; $[M+H]^+$=248.5.

2-Methyl-5-(3-trifluoromethyl-phenyl)-thiazole-4-carboxylic acid methyl ester prepared by reaction of 3-chloro-2-oxo-3-(3-trifluoromethyl-phenyl)-propionic acid methyl ester with thioacetamide. LC-MS: $t_R$=0.98 min; $[M+H]^+$=302.2.

5-(4-Bromo-phenyl)-2-methyl-thiazole-4-carboxylic acid methyl ester prepared by reaction of 3-(4-Bromo-phenyl)-3-chloro-2-oxo-propionic acid methyl ester with thioacetamide. LC-MS: $t_R$=0.95 min; $[M+H]^+$=312.2.

5-(3,5-Dimethyl-phenyl)-2-methyl-thiazole-4-carboxylic acid methyl ester prepared by reaction of 3-Chloro-3-(3,5-dimethyl-phenyl)-2-oxo-propionic acid methyl ester with thioacetamide. LC-MS: $t_R$=0.97 min; $[M+H]^+$=262.3.

5-(3-Bromo-4-fluoro-phenyl)-2-methyl-thiazole-4-carboxylic acid methyl ester prepared by reaction of 3-(3-Bromo-4-fluoro-phenyl)-3-chloro-2-oxo-propionic acid methyl ester with thioacetamide. LC-MS: $t_R$=0.95 min; $[M+H]^+$=330.2.

5-(3,4-Difluoro-phenyl)-2-methyl-thiazole-4-carboxylic acid methyl ester prepared by reaction of 3-Chloro-3-(3,4-difluoro-phenyl)-2-oxo-propionic acid methyl ester with thioacetamide. LC-MS: $t_R$=0.92 min; $[M+H]^+$=270.3.

5-(2,4-Dimethyl-phenyl)-2-methyl-thiazole-4-carboxylic acid methyl ester prepared by reaction of 3-Chloro-3-(2,4-dimethyl-phenyl)-2-oxo-propionic acid methyl ester with thioacetamide. LC-MS: $t_R$=0.96 min; $[M+H]^+$=262.3.

5-(3,4-Dichloro-phenyl)-2-methyl-thiazole-4-carboxylic acid methyl ester prepared by reaction of 3-Chloro-3-(3,4-dichloro-phenyl)-2-oxo-propionic acid methyl ester with thioacetamide. LC-MS: $t_R$=0.99 min; $[M+H]^+$=302.2.

5-(3,4-Dimethyl-phenyl)-2-methyl-thiazole-4-carboxylic acid methyl ester prepared by reaction of 3-Chloro-3-(3,4-dimethyl-phenyl)-2-oxo-propionic acid methyl ester with thioacetamide. LC-MS: $t_R$=0.96 min; [M+H]$^+$=262.3.

2-Methyl-5-phenyl-thiazole-4-carboxylic acid methyl ester prepared by reaction of 3-Chloro-2-oxo-3-phenyl-propionic acid methyl ester with thioacetamide. LC-MS: $t_R$=0.89 min; [M+H]$^+$=234.0.

2-Methyl-5-(3-nitro-phenyl)-thiazole-4-carboxylic acid methyl ester prepared by reaction of 3-Chloro-3-(3-nitro-phenyl)-2-oxo-propionic acid methyl ester with thioacetamide. LC-MS: $t_R$=0.94 min; [M+H]$^+$=279.3.

A.1.3 Synthesis of 2-amino-thiazole-4-carboxylic acid methyl ester Derivatives (General Procedure)

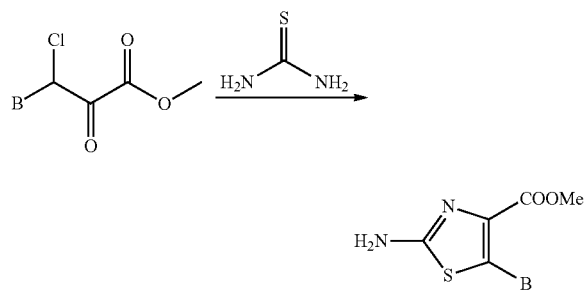

A solution of the respective α-oxo-ester (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24h and concentrated to half of the volume. The obtained suspension is filtered and the residue is washed with acetone. After drying the desired amino-thiazole derivative is obtained as a solid.

2-amino-5-p-tolyl-thiazole-4-carboxylic acid methyl ester prepared by reaction of 3-chloro-2-oxo-3-p-tolyl-propionic acid methyl ester with thiourea. LC-MS: $t_R$=0.77 min; [M+H]$^+$=249.3.

2-amino-5-(4-fluoro-phenyl)-thiazole-4-carboxylic acid methyl ester prepared by reaction of 3-chloro-3-(4-fluoro-phenyl)-2-oxo-propionic acid methyl ester with thiourea. LC-MS: $t_R$=0.75 min; [M+H]$^+$=253.2.

2-amino-5-(3-trifluoromethyl-phenyl)-thiazole-4-carboxylic acid methyl ester prepared by reaction of 3-chloro-3-(3-trifluoromethyl-phenyl)-2-oxo-propionic acid methyl ester with thiourea. LC-MS: $t_R$=0.86 min; [M+H]$^+$=303.3.

A.1.4 Synthesis of 2-bromo-thiazole-4-carboxylic acid methyl ester Derivatives (General Procedure)

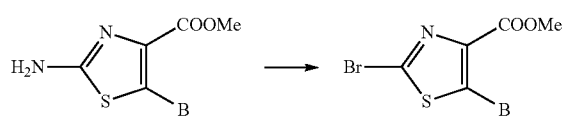

In an inert atmosphere, copper(II)bromide (69.6 mmol, 1.0 eq) was suspended in acetonitril (300 ml) and cooled to 5-10° C. followed by the addition of 3-methylbutylnitrite (104 mmol, 1.45 eq) over 15 min. To this reaction mixture the respective 2-aminothiazole derivative (70.0 mmol, 1 eq, free amine) was added in portions over 20 min. at 5-10° C. The reaction mixture was then carefully heated to 65° C. and stirring continued for 2 h. The volatiles were removed under reduced pressure and the residue was purified by column chromatography (silicagel; heptan/EtOAc or DCM/methanol, as the appropriate mixture) to give the respective product.

2-bromo-5-(4-fluoro-phenyl)-thiazole-4-carboxylic acid methyl ester prepared by reaction of 2-amino-5-(4-fluoro-phenyl)-thiazole-4-carboxylic acid methyl ester. LC-MS: $t_R$=0.97 min; [M+H]$^+$=316.1.

2-bromo-5-(3-trifluoromethyl-phenyl)-thiazole-4-carboxylic acid methyl ester prepared by reaction of 2-amino-5-(3-trifluoromethyl-phenyl)-thiazole-4-carboxylic acid methyl ester. LC-MS: $t_R$=1.04 min; [M+H]$^+$=366.2.

A.1.5 Synthesis of 2-cyclopropyl-thiazole-4-carboxylic acid methyl ester Derivatives (General Procedure I)

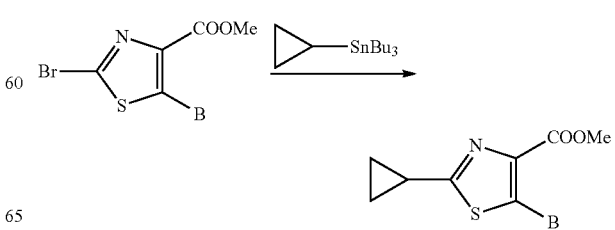

In an inert atmosphere, a solution of the respective 2-bromo-thiazole derivative (9.0 mmol, 1.0 eq) and of tributyl-cyclopropyl-stannane (9.9 mmol, 1.1 eq) in 1,2-dichloroethane (90 mL) is stirred for 5 min and treated with bis(triphenylphosphine)-palladium(II)chloride (0.45 mmol, 0.05eq). The mixture is heated to 80° C., stirred for 3 d and allowed to reach RT. DCM and water are added, the layers are separated and the aqueous layer is extracted once with DCM. The combined organic layers are dried over MgSO$_4$ and concentrated in vacuo. The residue is purified by column chromatography (silicagel; heptan/EtOAc, as the appropriate mixture) to give the desired product.

2-cyclopropyl-5-(4-fluoro-phenyl)-thiazole-4-carboxylic acid methyl ester prepared by cyclopropanation of 2-bromo-5-(4-fluoro-phenyl)-thiazole-4-carboxylic acid methyl ester. LC-MS: $t_R$=0.97 min; [M+H]$^+$=278.3.

2-cyclopropyl-5-(3-trifluoromethyl-phenyl)-thiazole-4-carboxylic acid methyl ester prepared by cyclopropanation of 2-bromo-5-(3-trifluoromethyl-phenyl)-thiazole-4-carboxylic acid methyl ester. LC-MS: $t_R$=1.03 min; [M+H]$^+$=328.2.

A.1.6 Synthesis of 2-cyclopropyl-thiazole-4-carboxylic acid methyl ester Derivatives (General Procedure II)

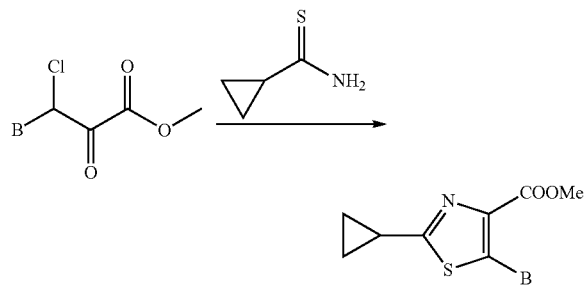

Synthesis of Cyclopropanecarbothioic acid amide 2,4-Bis-(4-methoxy-phenyl)-[1,3,2,4]dithiadiphosphetane-2,4-disulfide (Lawesson reagent, 115 mmol) is added to a mixture of cyclopropanecarboxamide (115 mmol) and sodium carbonate (115 mmol) in THF (500 mL). The mixture is heated to reflux for 2 h, the solvents are removed in vacuo and the residue is diluted with ether (500 mL) and water (500 mL). The layers are separated and the aqueous layer is extracted with ether (250 mL). The combined organic layers are washed with brine (100 mL), dried over MgSO$_4$ and concentrated in vacuo to give the desired thioamide which is used without further purification. LC-MS: $t_R$=0.39 min; [M+H+CH$_3$CN]$^+$=143.2.

Synthesis of 2-cyclopropyl-thiazole-4-carboxylic acid methyl ester Derivatives (General Procedure II)

A solution of cyclopropanecarbothioic acid amide (44.5 mmol, 1.0 eq) in MeCN (40 mL) is added to a mixture of the respective α-oxo-ester (44.5 mmol, 1.0 eq) and NaHCO$_3$ (134 mmol, 3.0 eq.) in MeCN (80 mL). After stirring for 16 h the mixture is concentrated in vacuo and the residue is diluted with EtOAc (200 mL) and water (200 mL). The layers are separated and the aqueous layer is extracted with EtOAc (100 mL). The combined organic layers are washed with brine (100 mL), dried over MgSO$_4$ and concentrated in vacuo. The crude product is dissolved in MeOH (90 mL) and treated with conc. H$_2$SO$_4$ (0.25 mL). The mixture is heated at 60° C. for 16 h and concentrated in vacuo to give the respective thiazole derivative.

2-Cyclopropyl-5-phenyl-thiazole-4-carboxylic acid methyl ester prepared by reaction of 3-Chloro-2-oxo-3-phenyl-propionic acid methyl ester with cyclopropanecarbothioic acid amide. LC-MS: $t_R$=0.99 min; [M+H]$^+$=260.5.

A.1.7 Synthesis of 5-(3-Acetylamino-phenyl)-2-methyl-thiazole-4-carboxylic acid methyl ester A.1.7.1 Synthesis of 5-(3-Amino-phenyl)-2-methyl-thiazole-4-carboxylic acid methyl ester A suspension of 2-methyl-5-(3-nitro-phenyl)-thiazole-4-carboxylic acid methyl ester (44.1 mmol) and ammonium chloride (220 mmol) in a mixture of ethanol (100 mL) and water (50 mL) is treated with iron powder (53.0 mmol) and heated to 80° C. After 4 h an additional portion of iron powder (53.0 mmol) is added, the mixture is stirred at 80° C. for 3 h, further iron powder (26.5 mmol) is added and the mixture is again stirred at 80° C. for 3.5 h. The mixture is allowed to reach RT, diluted with DCM and filtered through Celite. The filtrate is concentrated in vacuo and diluted with DCM and sat aqueous NaHCO$_3$ solution. The layers are separated and the organic layer is washed with water, dried over MgSO$_4$ and concentrated in vacuo to give the desired aniline derivative. LC-MS: $t_R$=0.67 min; [M+H]$^+$=249.4.

A.1.7.2 Synthesis of 5-(3-Acetylamino-phenyl)-2-methyl-thiazole-4-carboxylic acid methyl ester Triethylamine (14.2 mmol) and DMAP (4.00 mmol) are added to a solution of 5-(3-Amino-phenyl)-2-methyl-thiazole-4-carboxylic acid methyl ester (4.00 mmol) in acetic acid anhydride (25 mL). After 30 min EtOAc and water are added, the layers are separated and the aqueous layer is extracted once with EtOAc. The combined organic layers are washed twice with sat aqueous ammonium chloride solution, once with sat aqueous NaHCO$_3$ solution and once with water and the solvents are removed in vacuo. The residue is diluted with EtOAc and extracted three times with sat aqueous NaHCO$_3$ solution. The organic layer is dried over MgSO$_4$ and concentrated in vacuo to give a crude solid which is diluted with ether. The obtained suspension is filtered and the residue is washed with ether to give the desired acetamide. LC-MS: $t_R$=0.81 min; [M+H]$^+$=291.3.

A.1.8 Synthesis of thiazole-4-carboxylic acid Derivatives (General Procedure)

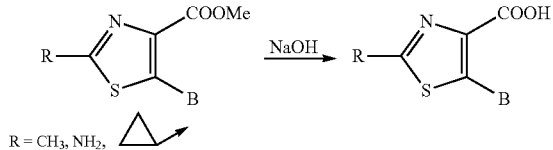

A solution of the respective ester (96.2 mmol) in a mixture of THF (150 mL) and MeOH (or isopropanol, 50 mL) is treated with an aqueous NaOH solution (1.0 M, 192 mL). After stirring for 3 h a white suspension is formed and the organic volatiles are removed in vacuo. The remaining mixture is diluted with water (100 mL), cooled in an ice-bath and made acidic (pH=3-4) by addition of aqueous HCl solution (1.0 M). In case of precipitation, the suspension is filtered and the residue is washed with cold water and dried in vacuo to give the desired acid. In other cases, the mixture is extracted twice with EtOAc and the organic layers are combined, dried over MgSO$_4$ and concentrated in vacuo to give the respective acid.

2-methyl-5-p-tolyl-thiazole-4-carboxylic acid prepared by saponification of 2-methyl-5-p-tolyl-thiazole-4-carboxylic acid methyl ester. LC-MS: $t_R$=0.83 min; $[M+H]^+$=234.0.

5-(3-fluoro-phenyl)-2-methyl-thiazole-4-carboxylic acid prepared by saponification of 5-(3-fluoro-phenyl)-2-methyl-thiazole-4-carboxylic acid methyl ester. LC-MS: $t_R$=0.82 min; $[M+H]^+$=238.1.

5-(4-fluoro-phenyl)-2-methyl-thiazole-4-carboxylic acid prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (br.s, 1H).

5-(3-chloro-phenyl)-2-methyl-thiazole-4-carboxylic acid prepared by saponification of 5-(3-chloro-phenyl)-2-methyl-thiazole-4-carboxylic acid methyl ester. LC-MS: $t_R$=0.84 min; $[M+H]^+$=254.0.

2-Methyl-5-m-tolyl-thiazole-4-carboxylic acid prepared by saponification of 2-Methyl-5-m-tolyl-thiazole-4-carboxylic acid methyl ester. LC-MS: $t_R$=0.87 min; $[M+H]^+$=234.4.

2-Methyl-5-(3-trifluoromethyl-phenyl)-thiazole-4-carboxylic acid prepared by saponification of 2-Methyl-5-(3-trifluoromethyl-phenyl)-thiazole-4-carboxylic acid methyl ester. LC-MS: $t_R$=0.88 min; $[M+H]^+$=288.0.

5-(4-Bromo-phenyl)-2-methyl-thiazole-4-carboxylic acid prepared by saponification of 5-(4-Bromo-phenyl)-2-methyl-thiazole-4-carboxylic acid methyl ester. LC-MS: $t_R$=0.85 min; $[M+H]^+$=298.2.

5-(3,5-Dimethyl-phenyl)-2-methyl-thiazole-4-carboxylic acid prepared by saponification of 5-(3,5-Dimethyl-phenyl)-2-methyl-thiazole-4-carboxylic acid methyl ester. LC-MS: $t_R$=0.86 min; $[M+H]^+$=248.3.

5-(3-Bromo-4-fluoro-phenyl)-2-methyl-thiazole-4-carboxylic acid prepared by saponification of 5-(3-Bromo-4-fluoro-phenyl)-2-methyl-thiazole-4-carboxylic acid methyl ester. LC-MS: $t_R$=0.86 min; $[M+H]^+$=316.2.

5-(3,4-Difluoro-phenyl)-2-methyl-thiazole-4-carboxylic acid prepared by saponification of 5-(3,4-Difluoro-phenyl)-2-methyl-thiazole-4-carboxylic acid methyl ester. LC-MS: $t_R$=0.82 min; $[M+H]^+$=256.3.

5-(2,4-Dimethyl-phenyl)-2-methyl-thiazole-4-carboxylic acid prepared by saponification of 5-(2,4-Dimethyl-phenyl)-2-methyl-thiazole-4-carboxylic acid methyl ester. LC-MS: $t_R$=0.85 min; $[M+H]^+$=248.3.

5-(3,4-Dichloro-phenyl)-2-methyl-thiazole-4-carboxylic acid prepared by saponification of 5-(3,4-Dichloro-phenyl)-2-methyl-thiazole-4-carboxylic acid methyl ester. LC-MS: $t_R$=0.88 min; $[M+H]^+$=288.2.

5-(3,4-Dimethyl-phenyl)-2-methyl-thiazole-4-carboxylic acid prepared by saponification of 5-(3,4-Dimethyl-phenyl)-2-methyl-thiazole-4-carboxylic acid methyl ester. LC-MS: $t_R$=0.86 min; $[M+H]^+$=248.3.

2-Methyl-5-phenyl-thiazole-4-carboxylic acid prepared by saponification of 2-Methyl-5-phenyl-thiazole-4-carboxylic acid methyl ester. LC-MS: $t_R$=0.77 min; $[M+H]^+$=220.0.

5-(3-Acetylamino-phenyl)-2-methyl-thiazole-4-carboxylic acid prepared by saponification of 5-(3-Acetylamino-phenyl)-2-methyl-thiazole-4-carboxylic acid methyl ester. LC-MS: $t_R$=0.73 min; [M+H]$^+$=277.2.

2-amino-5-p-tolyl-thiazole-4-carboxylic acid prepared by saponification of 2-amino-5-p-tolyl-thiazole-4-carboxylic acid methyl ester. LC-MS: $t_R$=0.64 min; [M+H]$^+$=235.2.

2-cyclopropyl-5-(4-fluoro-phenyl)-thiazole-4-carboxylic acid prepared by saponification of 2-cyclopropyl-5-(4-fluoro-phenyl)-thiazole-4-carboxylic acid methyl ester. LC-MS: $t_R$=0.87 min; [M+H]$^+$=264.2.

2-cyclopropyl-5-(3-trifluoromethyl-phenyl)-thiazole-4-carboxylic acid prepared by saponification of 2-cyclopropyl-5-(3-trifluoromethyl-phenyl)-thiazole-4-carboxylic acid methyl ester. LC-MS: $t_R$=0.94 min; [M+H]$^+$=314.2.

2-Cyclopropyl-5-phenyl-thiazole-4-carboxylic acid prepared by saponification of 2-Cyclopropyl-5-phenyl-thiazole-4-carboxylic acid. LC-MS: $t_R$=0.91 min; [M+H]$^+$=246.4.

A.2 Synthesis of 2,3-dihydro-benzofuran-4-carboxylic acid

Benzofuran-4-carboxylic acid (30.8 mmol, M. A. Eissenstat et al. *J. Med. Chem.* 1995, 38, 3094-3105) is added to a suspension of Pd/C (10%, 2.00 g) in EtOH (25 mL). Additional EtOH (75 mL) is added and the mixture is stirred at RT under a hydrogen atmosphere (4 bar) for 16 h. After filtration through celite and removal of the solvents the desired product is obtained which is used without further purification. $^1$H-NMR (DMSO-d$_6$): δ=3.45 (t, J=8.79 Hz, 2H); 4.55 (t, J=8.79 Hz, 2H); 6.99 (d, J=7.78 Hz, 1H); 7.21 (t, J=7.91 Hz, 1H); 7.39 (d, J=7.78 Hz, 1H); 12.9 (bs, 1H).

A.3 Synthesis of (1S,3S,5S)-3-aminomethyl-2-azabicyclo[3.3.0]octane-2-carboxylic acid tert-butyl ester

A.3.1 Synthesis of (1S,3S,5S)-(2-tert-butoxy-carbonyl)-2-azabicyclo[3.3.0]octane-3-carboxylic acid benzyl ester To a suspension of Benzyl (1S,3S,5S)-2-azabicyclo[3.3.0]octane-3-carboxylate hydrochloride (17.3 mmol, 1.0 eq) in DCM (50 mL) is added DIPEA (22.5 mmol, 1.3 eq), di-tert-butyl dicarbonate (17.3 mmol, 1.0 eq) and additional DCM (5 mL). The mixture is stirred for 1 h and concentrated in vacuo. EtOAc and aqueous citric acid (10%) are added, the layers are separated and the aqueous layer is extracted once with EtOAc. The combined organic layers are washed with brine, dried over MgSO$_4$ and concentrated in vacuo. The residue is purified by column chromatography (heptane/EtOAc 3/1) to give the desired product. LC-MS: $t_R$=1.08 min; [M+H]$^+$=346.3.

A.3.2 Synthesis of (1S,3S,5S)-3-hydroxymethyl-2-azabicyclo[3.3.0]octane-2-carboxylic acid tert-butyl ester At −78° C. a solution of DIBAL in toluene (1.7 M, 22.5 mmol) is added dropwise to a solution of (1S,3S,5S)-(2-tert-butoxy-carbonyl)-2-azabicyclo [3.3.0]octane-3-carboxylic acid benzyl ester (9.0 mmol) in THF (50 mL). After 40 min the mixture is allowed to reach RT, stirred for additional 45 min and poured into a mixture of aqueous NaOH solution (1.0 M, 250 mL) and ice. EtOAc is added, the layers are separated and the aqueous layer is extracted with EtOAc. The combined organic layers are washed with aqueous NaOH solution (1.0 M) and brine, dried over MgSO$_4$ and concentrated in vacuo to give the desired alcohol which is purified by flash chromatography (heptane/EtOAc 3/1). LC-MS: $t_R$=0.91 min; [M+H]$^+$=242.4.

A.3.3 Synthesis of (1S,3S,5S)-3-formyl-2-azabicyclo[3.3.0]octane-2-carboxylic acid tert-butyl ester A solution of Dess-Martin periodinane (4.14 mmol, 2.2 eq) in DCM (10 ml) is treated with a solution of (1S,3S,5S)-3-hydroxymethyl-2-azabicyclo[3.3.0]octane-2-carboxylic acid tert-butyl ester (1.85 mmol, 1.0 eq) in DCM (4 mL) and some drops of water. After 5 h ether and aqueous NaOH solution (1.0 M) are added and the layers are separated. The organic layer is washed with aqueous citric acid (10%) and brine, dried over MgSO$_4$ and concentrated in vacuo to give the desired aldehyde which is used without further purification.

A.3.4 Synthesis of (1S,3S,5S)-3-(benzylamino-methyl)-2-azabicyclo[3.3.0]octane-2-carboxylic acid tert-butyl ester Benzylamine (2.76 mmol, 2.3 eq) is added to a solution of (1S,3S,5S)-3-formyl-2-azabicyclo[3.3.0]octane-2-carboxylic acid tert-butyl ester (1.2 mmol, 1.0 eq) in chloroform (10 mL). The mixture is stirred for 5 min, treated with sodium triacetoxyborohydride (4.8 mmol, 4.0 eq) and acetic acid (0.05 mL), stirred for additional 14 h and poured into sat. NaHCO$_3$ solution. DCM is added, the layers are separated and the aqueous layer is extracted with DCM. The combined organic layers are washed with water (100 mL) and concentrated in vacuo. The residue is dissolved in ether and extracted three times with hydrochloric acid (0.1 M). The combined aqueous layers are extracted once with ether, made basic (pH 9-10) by addition of NaOH solution (1.0M) and extracted three times with ether. The combined organic layers are dried over MgSO$_4$ and concentrated in vacuo to give the desired benzylamine which is used without further purification. LC-MS: $t_R$=0.89 min; [M+H]$^+$=331.5.

A.3.5 Synthesis of (1S,3S,5S)-3-aminomethyl-2-azabicyclo[3.3.0]octane-2-carboxylic acid tert-butyl ester A solution of (1S,3S,5S)-3-(benzylamino-methyl)-2-azabicyclo[3.3.0]octane-2-carboxylic acid tert-butyl ester (9.0 mmol) in ethanol (10 mL) is added to a suspension of Pd/C (1.9 g, 10%) in ethanol (40 mL) and stirred under a hydrogen atmosphere (1 bar) for 16 h. After filtration through celite, washing with ethanol and removal of the solvents the desired amine is obtained which is used without further purification. LC-MS: $t_R$=0.73 min; [M+H]$^+$=241.4.

A.4 Synthesis of (1S,3S,5S)-(2-azabicyclo[3.3.0]octane-3-ylmethyl)-amide derivatives

A.4.1 Synthesis of (1S,3S,5S)-3-(aroylamino-methyl)-2-azabicyclo[3.3.0]octane-2-carboxylic acid tert-butyl ester (General Procedure)

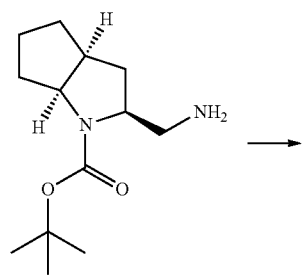

TBTU (5.0 mmol, 1.2 eq) is added to a solution of the respective carboxylic acid (4.6 mmol, 1.1 eq) in DMF (15 mL). After 30 min DIPEA (12.5 mmol, 3.0 eq) and a solution of (1S,3S,5S)-3-aminomethyl-2-azabicyclo[3.3.0]octane-2-carboxylic acid tert-butyl ester (4.2 mmol, 1.0 eq) in DMF (10 mL) are added and the mixture is stirred for 60 min. Water and EtOAc are added, the layers are separated and the organic layer is washed once with water. The combined aqueous layers are extracted once with EtOAc and the combined organic layers are dried over MgSO$_4$. The solvents are removed in vacuo and the residue is purified by column chromatography (DCM) to give the respective amide.

(1S,3S,5S)-3-{[(6-methyl-imidazo[2,1-b]thiazole-5-carbonyl)-amino]-methyl}-2-azabicyclo[3.3.0]octane-2-carboxylic acid tert-butyl ester prepared by reaction of 6-methyl-imidazo[2,1-b]thiazole-5-carboxylic acid (A. Andreani et al. *Eur. J. Med. Chem* 1982, 17, 271-274) with (1S,3S,5S)-3-aminomethyl-2-azabicyclo[3.3.0]octane-2-carboxylic acid tert-butyl ester. LC-MS: $t_R$=0.91 min; [M+H]$^+$=405.2.

(1S,3S,5S)-3-{[(Benzo[d]isoxazole-3-carbonyl)-amino]methyl}-2-azabicyclo[3.3.0]octane-2-carboxylic acid tert-butyl ester prepared by reaction of Benzo[d]isoxazole-3-carboxylic acid with (1S,3S,5S)-3-aminomethyl-2-azabicyclo[3.3.0]octane-2-carboxylic acid tert-butyl ester. LC-MS: $t_R$=1.11 min; [M+H]$^+$=386.6.

(1S,3S,5S)-3-{[(2,3-Dihydro-benzofuran-4-carbonyl)-amino]-methyl}-2-azabicyclo[3.3.0]octane-2-carboxylic acid tert-butyl ester prepared by reaction of 2,3-Dihydro-benzofuran-4-carboxylic acid with (1S,3S,5S)-3-aminomethyl-2-azabicyclo[3.3.0]octane-2-carboxylic acid tert-butyl ester. LC-MS: $t_R$=1.00 min; [M+H]$^+$=387.1.

A.4.2 Synthesis of (1S,3S,5S)-(2-azabicyclo[3.3.0]octane-3-ylmethyl)-amide Derivatives (General Procedure)

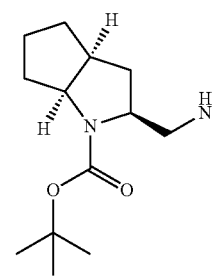

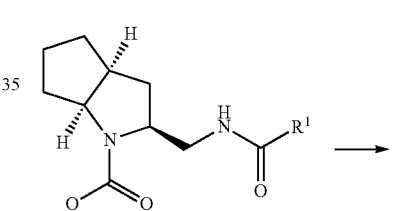

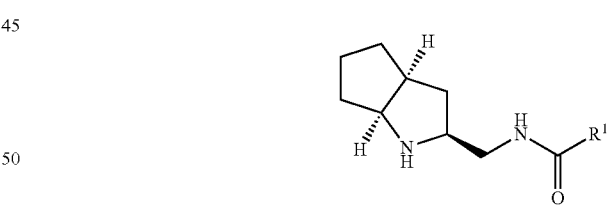

A solution of HCl in dioxane (4.0 M, 20 mL) is added to a solution of the respective Boc-protected 2-azabicyclo[3.3.0]octane derivative (3.6 mmol) in dioxane (20 mL). After LC-MS indicated complete reaction (1-3 h) the mixture is concentrated in vacuo to give the respective deprotected product which is used without further purification.

6-methyl-imidazo[2,1-b]thiazole-5-carboxylic acid [(1S,3S,5S)-(2-azabicyclo[3.3.0]octane-3-yl)methyl]-amide prepared by deprotection of (1S,3S,5S)-3-{[(6-methyl-imidazo[2,1-b]thiazole-5-carbonyl)-amino]-methyl}-2- azabicyclo[3.3.0]octane-2-carboxylic acid tert-butyl ester. LC-MS: $t_R$=0.56 min; [M+H]$^+$=305.3.

Benzo[d]isoxazole-3-carboxylic acid [(1S,3S,5S)-(2-azabicyclo[3.3.0]octane-3-yl)methyl]-amide prepared by deprotection of (1S,3S,5S)-3-{[(Benzo[d]isoxazole-3-carbonyl)-amino]-methyl}-2-azabicyclo[3.3.0]octane-2-carboxylic acid tert-butyl ester. LC-MS: $t_R$=0.71 min; [M+H]$^+$=286.3.

2,3-Dihydro-benzofuran-4-carboxylic acid [(1S,3S,5S)-(2-azabicyclo[3.3.0]octane-3-yl)methyl]-amide prepared by deprotection of (1S,3S,5S)-3-{[(2,3-Dihydro-benzofuran-4-carbonyl)-amino]-methyl}-2-azabicyclo[3.3.0]octane-2-carboxylic acid tert-butyl ester. LC-MS: $t_R$=0.70 min; [M+H]$^+$=287.4.

B. Preparation of Compounds of Formula (I):

B.1 Synthesis of carboxylic amide Derivatives (General Procedure)

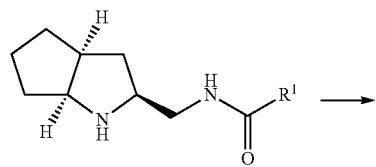

→

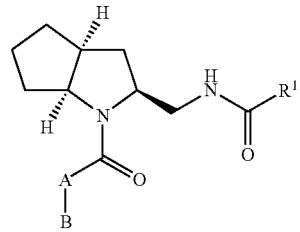

To a mixture of the respective carboxylic acid (0.44 mmol, 1.1 eq) in acetonitrile (1.0 mL) is added TBTU (0.48 mmol, 1.2 eq) and, after 30 min, DIPEA (1.2 mmol, 3.0 eq). After 15 min a solution of the respective 2-azabicyclo[3.3.0]octane derivative (0.40 mmol, 1.0 eq) in DCM (1.0 mL) is added. The mixture is stirred over night and purified by prep. HPLC to give the respective amide derivative.

Synthesis of carboxylic amide derivatives by reaction of the respective carboxylic acid with 6-methyl-imidazo[2,1-b]thiazole-5-carboxylic acid [(1S,3S,5S)-(2-azabicyclo[3.3.0]octane-3-yl)methyl]-amide:

| Example | Name | LC-MS: |
|---|---|---|
| 1 | 6-Methyl-imidazo[2,1-b]thiazole-5-carboxylic acid [(1S,3S,5S)-2-(2-methyl-5-p-tolyl-thiazole-4-carbonyl)-2-azabicyclo[3.3.0]octane-3-ylmethyl]-amide | $t_R$ = 0.95 min; [M + H]$^+$ = 520.1 |
| 2 | 6-Methyl-imidazo[2,1-b]thiazole-5-carboxylic acid [(1S,3S,5S)-2-(2-amino-5-p-tolyl-thiazole-4-carbonyl)-2-azabicyclo[3.3.0]octane-3-ylmethyl]-amide | $t_R$ = 0.86 min; [M + H]$^+$ = 521.2 |
| 3 | 6-Methyl-imidazo[2,1-b]thiazole-5-carboxylic acid {(1S,3S,5S)-2-[5-(3-chloro-phenyl)-2-methyl-thiazole-4-carbonyl]-2-azabicyclo[3.3.0]octane-3-ylmethyl}-amide | $t_R$ = 0.95 min; [M + H]$^+$ = 540.1 |
| 4 | 6-Methyl-imidazo[2,1-b]thiazole-5-carboxylic acid {(1S,3S,5S)-2-[5-(4-fluoro-phenyl)-2-methyl-thiazole-4-carbonyl]-2-azabicyclo[3.3.0]octane-3-ylmethyl}-amide | $t_R$ = 0.93 min; [M + H]$^+$ = 524.2 |
| 5 | 6-Methyl-imidazo[2,1-b]thiazole-5-carboxylic acid {(1S,3S,5S)-2-[5-(3-fluoro-phenyl)-2-methyl-thiazole-4-carbonyl]-2-azabicyclo[3.3.0]octane-3-ylmethyl}-amide | $t_R$ = 0.93 min; [M + H]$^+$ = 524.2 |
| 6 | 6-Methyl-imidazo[2,1-b]thiazole-5-carboxylic acid {(1S,3S,5S)-2-[2-cyclopropyl-5-(4-fluoro-phenyl)-thiazole-4-carbonyl]-2-azabicyclo[3.3.0]octane-3-ylmethyl}-amide | $t_R$ = 0.99 min; [M + H]$^+$ = 550.4 |
| 7 | 6-Methyl-imidazo[2,1-b]thiazole-5-carboxylic acid {(1S,3S,5S)-2-[2-cyclopropyl-5-(3-trifluoromethyl-phenyl)-thiazole-4-carbonyl]-2-azabicyclo[3.3.0]octane-3-ylmethyl}-amide | $t_R$ = 1.04 min; [M + H]$^+$ = 600.2 |

Synthesis of carboxylic amide derivatives by reaction of the respective carboxylic acid with benzo[d]isoxazole-3-carboxylic acid [(1S,3S,5S)-(2-azabicyclo[3.3.0]octane-3-yl)methyl]-amide:

| Example | Name | LC-MS: |
|---|---|---|
| 8 | Benzo[d]isoxazole-3-carboxylic acid [(1S,3S,5S)-2-(2-methyl-5-p-tolyl-thiazole-4-carbonyl)-2-azabicyclo[3.3.0]octane-3-ylmethyl]-amide | $t_R$ = 1.09 min; [M + H]$^+$ = 501.2 |
| 9 | Benzo[d]isoxazole-3-carboxylic acid {(1S,3S,5S)-2-[5-(3-chloro-phenyl)-2-methyl-thiazole-4-carbonyl]-2-azabicyclo[3.3.0]octane-3-ylmethyl}-amide | $t_R$ = 1.10 min; [M + H]$^+$ = 521.1 |
| 10 | Benzo[d]isoxazole-3-carboxylic acid {(1S,3S,5S)-2-[5-(3-fluoro-phenyl)-2-methyl-thiazole-4-carbonyl]-2-azabicyclo[3.3.0]octane-3-ylmethyl}-amide | $t_R$ = 1.08 min; [M + H]$^+$ = 505.2 |
| 11 | Benzo[d]isoxazole-3-carboxylic acid [(1S,3S,5S)-2-(2-cyclopropyl-5-phenyl-thiazole-4-carbonyl)-2-azabicyclo[3.3.0]octane-3-ylmethyl]-amide | $t_R$ = 1.12 min; [M + H]$^+$ = 512.8 |

Synthesis of carboxylic amide derivatives by reaction of the respective carboxylic acid with 2,3-Dihydro-benzofuran-4-carboxylic acid [(1S,3S,5S)-(2-azabicyclo[3.3.0]octane-3-yl)methyl]-amide:

| Example | Name | LC-MS: |
|---|---|---|
| 12 | 2,3-Dihydro-benzofuran-4-carboxylic acid {(1S,3S,5S)-2-[5-(3-chloro-phenyl)-2-methyl-thiazole-4-carbonyl]-2-azabicyclo[3.3.0]octane-3-ylmethyl}-amide | $t_R$ = 1.05 min; [M + H]$^+$ = 522.1 |
| 13 | 2,3-Dihydro-benzofuran-4-carboxylic acid {(1S,3S,5S)-2-[5-(3-fluoro-phenyl)-2-methyl-thiazole-4-carbonyl]-2-azabicyclo[3.3.0]octane-3-ylmethyl}-amide | $t_R$ = 1.02 min; [M + H]$^+$ = 506.1 |
| 14 | 2,3-Dihydro-benzofuran-4-carboxylic acid {(1S,3S,5S)-2-[5-(4-fluoro-phenyl)-2-methyl-thiazole-4-carbonyl]-2-azabicyclo[3.3.0]octane-3-ylmethyl}-amide | $t_R$ = 1.02 min; [M + H]$^+$ = 506.1 |
| 15 | 2,3-Dihydro-benzofuran-4-carboxylic acid [(1S,3S,5S)-2-(2-methyl-5-m-tolyl-thiazole-4-carbonyl)-2-azabicyclo[3.3.0]octane-3-ylmethyl]-amide | $t_R$ = 1.04 min; [M + H]$^+$ = 502.2 |
| 16 | 2,3-Dihydro-benzofuran-4-carboxylic acid {(1S,3S,5S)-2-[2-methyl-5-(3-trifluoromethyl-phenyl)-thiazole-4-carbonyl]-2-azabicyclo[3.3.0]octane-3-ylmethyl}-amide | $t_R$ = 1.07 min; [M + H]$^+$ = 556.2 |
| 17 | 2,3-Dihydro-benzofuran-4-carboxylic acid {(1S,3S,5S)-2-[5-(4-bromo-phenyl)-2-methyl-thiazole-4-carbonyl]-2-azabicyclo[3.3.0]octane-3-ylmethyl}-amide | $t_R$ = 1.06 min; [M + H]$^+$ = 566.1 |
| 18 | 2,3-Dihydro-benzofuran-4-carboxylic acid {(1S,3S,5S)-2-[5-(3,5-dimethyl-phenyl)-2-methyl-thiazole-4-carbonyl]-2-azabicyclo[3.3.0]octane-3-ylmethyl}-amide | $t_R$ = 1.07 min; [M + H]$^+$ = 516.2 |
| 19 | 2,3-Dihydro-benzofuran-4-carboxylic acid {(1S,3S,5S)-2-[5-(3-bromo-4-fluoro-phenyl)-2-methyl-thiazole-4-carbonyl]-2-azabicyclo[3.3.0]octane-3-ylmethyl}-amide | $t_R$ = 1.06 min; [M + H]$^+$ = 584.1 |
| 20 | 2,3-Dihydro-benzofuran-4-carboxylic acid {(1S,3S,5S)-2-[5-(3,4-difluoro-phenyl)-2-methyl-thiazole-4-carbonyl]-2-azabicyclo[3.3.0]octane-3-ylmethyl}-amide | $t_R$ = 1.04 min; [M + H]$^+$ = 524.2 |
| 21 | 2,3-Dihydro-benzofuran-4-carboxylic acid {(1S,3S,5S)-2-[5-(2,4-dimethyl-phenyl)-2-methyl-thiazole-4-carbonyl]-2-azabicyclo[3.3.0]octane-3-ylmethyl}-amide | $t_R$ = 1.08 min; [M + H]$^+$ = 516.2 |
| 22 | 2,3-Dihydro-benzofuran-4-carboxylic acid {(1S,3S,5S)-2-[5-(3,4-dichloro-phenyl)-2-methyl-thiazole-4-carbonyl]-2-azabicyclo[3.3.0]octane-3-ylmethyl}-amide | $t_R$ = 1.09 min; [M + H]$^+$ = 556.1 |
| 23 | 2,3-Dihydro-benzofuran-4-carboxylic acid {(1S,3S,5S)-2-[5-(3,4-dimethyl-phenyl)-2-methyl-thiazole-4-carbonyl]-2-azabicyclo[3.3.0]octane-3-ylmethyl}-amide | $t_R$ = 1.07 min; [M + H]$^+$ = 516.2 |
| 24 | 2,3-Dihydro-benzofuran-4-carboxylic acid {(1S,3S,5S)-2-[5-(3-acetylamino-phenyl)-2-methyl-thiazole-4-carbonyl]-2-azabicyclo[3.3.0]octane-3-ylmethyl}-amide | $t_R$ = 0.92 min; [M + H]$^+$ = 545.2 |
| 25 | 2,3-Dihydro-benzofuran-4-carboxylic acid [(1S,3S,5S)-2-(2-methyl-5-phenyl-thiazole-4-carbonyl)-2-azabicyclo[3.3.0]octane-3-ylmethyl]-amide | $t_R$ = 1.01 min; [M + H]$^+$ = 488.2 |
| 26 | 2,3-Dihydro-benzofuran-4-carboxylic acid [(1S,3S,5S)-2-(2-cyclopropyl-5-phenyl-thiazole-4-carbonyl)-2-azabicyclo[3.3.0]octane-3-ylmethyl]-amide | $t_R$ = 1.07 min; [M + H]$^+$ = 514.1 |

II—Biological Assays

The orexin receptor antagonistic activity of the compounds of formula (I) is determined in accordance with the following experimental method.

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH: water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at rt for 30-120 min before measurement.

Within the Fluorescent Imaging Plate Reader (FLIPR2 or FLIPR Tetra, Molecular Devices), antagonists are added to the plate in a volume of 10 µl/well, incubated for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the $IC_{50}$ value (the concentration of compound needed to inhibit 50% of the agonistic response) is determined. The calculated $IC_{50}$ values of the compounds may fluctuate depending on the daily cellular assay performance. Fluctuations of this kind are known to those skilled in the art.

$IC_{50}$ values of 26 exemplified compounds are in the range of 4-2438 nM with respect to the $OX_1$ receptor. $IC_{50}$ values of all exemplified compounds are in the range of 11-1669 nM with respect to the $OX_2$ receptor. Antagonistic activities of selected compounds are displayed in Table 1.

TABLE 1

| Example | $OX_1$ $IC_{50}$ (nM) | $OX_2$ $IC_{50}$ (nM) |
|---|---|---|
| 1 | 17 | 40 |
| 7 | 18 | 95 |
| 9 | 275 | 283 |
| 16 | 11[1] | 12[1] |
| 19 | 37[1] | 32[1] |
| 26 | 48[1] | 41[1] |

Values in table 1 are measured using FLIPR2 or using [1] FLIPR Tetra.

The invention claimed is:
1. A compound of formula (I) with the stereogenic centers in (1S,3S,5S)-configuration

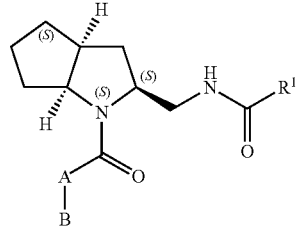

Formula (I)

wherein
A represents aryl or heterocyclyl, wherein the aryl or heterocyclyl is unsubstituted or independently mono- or disubstituted, wherein the substituents are independently selected from the group consisting of $(C_{1-4})$alkyl, $(C_{3-6})$cycloalkyl, $(C_{2-6})$alkinyl, $(C_{1-4})$alkoxy, $NR^2R^3$, halogen and independently mono- or disubstituted phenyl, wherein the substituents are independently selected from the group consisting of $(C_{1-4})$ alkyl, $(C_{1-4})$alkoxy, fluorine and chlorine;
B represents an aryl- or heterocyclyl-group, wherein the aryl or heterocyclyl is unsubstituted or independently mono-, di-, or trisubstituted, wherein the substituents are independently selected from the group consisting of $(C_{1-4})$alkyl, $(C_{1-4})$alkoxy, trifluoromethyl, $NR^2R^3$, $NHC(O)CH_3$ and halogen;
$R^1$ represents aryl or heterocyclyl, wherein the aryl or heterocyclyl is unsubstituted or independently mono-, di-, or trisubstituted wherein the substituents are independently selected from the group consisting of $(C_{1-4})$ alkyl, $(C_{1-4})$alkoxy, halogen, trifluoromethyl and $NR^2R^3$; or $R^1$ represents a 2,3-dihydro-benzofuranyl- or a 2,3-dihydro-benzo[1,4]dioxinyl-group which groups are unsubstituted or independently mono- or disubstituted with $(C_{1-4})$alkyl, $(C_{1-4})$alkoxy and halogen;
$R^2$ represents hydrogen or $(C_{1-4})$alkyl;
$R^3$ represents hydrogen or $(C_{1-4})$alkyl;
or a pharmaceutically acceptable salt thereof.
2. A compound according to claim 1, wherein
A represents heterocyclyl, wherein the heterocyclyl is unsubstituted or mono-sub-stituted, wherein the substituent is selected from the group consisting of $(C_{1-4})$ alkyl, $(C_{3-6})$cycloalkyl or $NR^2R^3$; or a pharmaceutically acceptable salt thereof.
3. A compound according to claim 1, wherein
B represents aryl, wherein the aryl is unsubstituted or independently mono- or disubstituted, wherein the substituents are independently selected from the group consisting of $(C_{1-4})$alkyl, $(C_{1-4})$alkoxy, trifluoromethyl, $NHC(O)CH_3$ and halogen;
or a pharmaceutically acceptable salt thereof.
4. A compound according to claim 1, wherein
$R^1$ represents aryl or heterocyclyl, wherein the aryl or heterocyclyl is unsubstituted or independently mono- or disubstituted wherein the substituents are independently selected from the group consisting of $(C_{1-4})$alkyl, $(C_{1-4})$ alkoxy and halogen; or $R^1$ represents a 2,3-dihydro-benzofuranyl- or a 2,3-dihydro-benzo[1,4]dioxinyl-group;
or a pharmaceutically acceptable salt thereof.

5. A compound according to claim 1, wherein
A represents an oxazolyl, a thiazolyl or a pyrimidyl group, which groups are unsubstituted or monosubstituted, wherein the substituent is selected from the group consisting of $(C_{1-4})$alkyl, $(C_{3-6})$cycloalkyl or $NH_2$;
or a pharmaceutically acceptable salt thereof.

6. A compound according to claim 1, wherein
B represents phenyl, wherein the phenyl is unsubstituted or independently mono- or disubstituted, wherein the substituents are independently selected from the group consisting of $(C_{1-4})$alkyl, trifluoromethyl and halogen;
or a pharmaceutically acceptable salt thereof.

7. A compound according to claim 1, wherein
$R^1$ represents an imidazo[2,1-b]thiazolyl or a benzoisoxazolyl group which groups are unsubstituted or monosubstituted wherein the substituent is selected from the group consisting of $(C_{1-4})$alkyl, trifluoromethyl and halogen; or $R^1$ represents a 2,3-dihydro-benzofuranyl-group;
or a pharmaceutically acceptable salt thereof.

8. A compound according to claim 1, wherein
A represents a thiazolyl group, which group is unsubstituted or monosubstituted, wherein the substituent is selected from the group consisting of $(C_{1-4})$alkyl, $(C_{3-6})$cycloalkyl or $NH_2$;
or a pharmaceutically acceptable salt thereof.

9. A compound according to claim 1, wherein
$R^2$ and $R^3$ both represent hydrogen;
or a pharmaceutically acceptable salt thereof.

10. A compound according to claim 1 selected from the group consisting of:
6-Methyl-imidazo[2,1-b]thiazole-5-carboxylic acid [(1S,3S,5S)-2-(2-methyl-5-p-tolyl-thiazole-4-carbonyl)-2-azabicyclo[3.3.0]octane-3-ylmethyl]-amide;
6-Methyl-imidazo[2,1-b]thiazole-5-carboxylic acid [(1S,3S,5S)-2-(2-amino-5-p-tolyl-thiazole-4-carbonyl)-2-azabicyclo[3.3.0]octane-3-ylmethyl]-amide;
6-Methyl-imidazo[2,1-b]thiazole-5-carboxylic acid {(1S,3S,5S)-2-[5-(3-chloro-phenyl)-2-methyl-thiazole-4-carbonyl]-2-azabicyclo[3.3.0]octane-3-ylmethyl}-amide;
6-Methyl-imidazo[2,1-b]thiazole-5-carboxylic acid {(1S,3S,5S)-2-[5-(4-fluoro-phenyl)-2-methyl-thiazole-4-carbonyl]-2-azabicyclo[3.3.0]octane-3-ylmethyl}-amide;
6-Methyl-imidazo[2,1-b]thiazole-5-carboxylic acid {(1S,3S,5S)-2-[5-(3-fluoro-phenyl)-2-methyl-thiazole-4-carbonyl]-2-azabicyclo[3.3.0]octane-3-ylmethyl}-amide;
6-Methyl-imidazo[2,1-b]thiazole-5-carboxylic acid {(1S,3S,5S)-2-[2-cyclopropyl-5-(4-fluoro-phenyl)-thiazole-4-carbonyl]-2-azabicyclo[3.3.0]octane-3 -ylmethyl}-amide;
6-Methyl-imidazo[2,1-b]thiazole-5-carboxylic acid {(1S,3S,5S)-2-[2-cyclopropyl-5-(3-trifluoromethyl-phenyl)-thiazole-4-carbonyl]-2-azabicyclo[3.3.0]octane-3-ylmethyl}-amide;
Benzo[d]isoxazole-3-carboxylic acid [(1S,3S,5S)-2-(2-methyl-5-p-tolyl-thiazole-4-carbonyl)-2-azabicyclo[3.3.0]octane-3-ylmethyl]-amide;
Benzo[d]isoxazole-3-carboxylic acid {(1S,3S,5S)-2[5-(3-chloro-phenyl)-2-methyl-thiazole-4-carbonyl]-2-azabicyclo[3.3.0]octane-3-ylmethyl}-amide;
Benzo[d]isoxazole-3-carboxylic acid {(1S,3S,5S)-2-[5-(3-fluoro-phenyl)-2-methyl-thiazole-4-carbonyl]-2-azabicyclo[3.3.0]octane-3-ylmethyl}-amide;
Benzo[d]isoxazole-3-carboxylic acid [(1S,3S,5S)-2-(2-cyclopropyl-5-phenyl-thiazole-4-carbonyl)-2-azabicyclo[3.3.0]octane-3-ylmethyl]-amide;
2,3-Dihydro-benzofuran-4-carboxylic acid {(1S,3S,5S)-2-[5-(3-chloro-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3-fluoro-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(4-fluoro-phenyl)-2-methyl-thiazole-4-carbonyl]-2-azabicyclo[3.3.0]octane-3-ylmethyl}-amide;
2,3-Dihydro-benzofuran-4-carboxylic acid [(1S,3S,5S)-2-(2-methyl-5-m-tolyl-thiazole-4-carbonyl)-2-azabicyclo[3.3.0]octane-3-ylmethyl]-amide;
2,3-Dihydro-benzofuran-4-carboxylic acid {(1S,3S,5S)-2-[2-methyl-5-(3-trifluoromethyl-phenyl)-thiazole-4-carbonyl]-2-azabicyclo[3.3.0]octane-3 -ylmethyl}-amide;
2,3-Dihydro-benzofuran-4-carboxylic acid {(1S,3S,5S)-2-[5-(4-bromo-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3,5-dimethyl-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3-bromo-4-fluoro-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3,4-difluoro-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(2,4-dimethyl-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3,4-dichloro-phenyl)-2-methyl-thiazole-4-carbonyl]-2-azabicyclo [3.3.0]octane-3-ylmethyl}-amide;
2,3-Dihydro-benzofuran-4-carboxylic acid {(1S,3S,5S)-2-[5-(3,4-dimethyl-phenyl)-2-methyl-thiazole-4-carbonyl]-2-azabicyclo[3.3.0]octane-3-ylmethyl}-amide;
2,3-Dihydro-benzofuran-4-carboxylic acid {(1S,3S,5S)-2-[5-(3-acetylamino-phenyl)-2-methyl-thiazole-4-carbonyl]-2-azabicyclo[3.3.0]octane-3-ylmethyl}-amide;
2,3-Dihydro-benzofuran-4-carboxylic acid [(1S,3S,5S)-2-(2-methyl-5-phenyl-thiazole-4-carbonyl)-2-azabicyclo[3.3.0]octane-3-ylmethy]-amide; and
2,3-Dihydro-benzofuran-4-carboxylic acid [(1S,3S,5S)-2-(2-cyclopropyl-5-phenyl-thiazole-4-carbonyl)-2-azabicyclo[3.3.0]octane-3-ylmethyl]-amide;
or a pharmaceutically acceptable salt thereof.

11. A pharmaceutical composition comprising a compound of claim 1, in free or a pharmaceutically acceptable salt form, and at least one therapeutically inert excipient.

12. A compound according to claim 1 in the form of a pharmaceutically acceptable salt.

13. A method for the treatment of sleep disorders selected from the group consisting insomnias, restless leg syndrome, jet-lag syndrome, shift-work syndrome, delayed or advanced sleep phase syndrome, and insomnias related to psychiatric disorders, comprising administering the compound of claim 1, in free or pharmaceutically acceptable salt form to a subject in need of such prophylaxis or treatment.

* * * * *